US012746278B2

(12) United States Patent
Eliceiri et al.

(10) Patent No.: US 12,746,278 B2
(45) Date of Patent: Sep. 29, 2026

(54) COMPOSITIONS AND METHODS FOR WOUND HEALING

(71) Applicant: The Regents of the University of California, Oakland, CA (US)

(72) Inventors: Brian P. Eliceiri, Carlsbad, CA (US); Dong Jun Park, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 161 days.

(21) Appl. No.: 18/722,579

(22) PCT Filed: Dec. 20, 2022

(86) PCT No.: PCT/US2022/053560

§ 371 (c)(1),
(2) Date: Jun. 20, 2024

(87) PCT Pub. No.: WO2023/122120

PCT Pub. Date: Jun. 29, 2023

(65) Prior Publication Data

US 2025/0049898 A1 Feb. 13, 2025

Related U.S. Application Data

(60) Provisional application No. 63/292,966, filed on Dec. 22, 2021.

(51) Int. Cl.
*A61K 38/57* (2006.01)
*A61K 9/50* (2006.01)
*A61P 17/02* (2006.01)

(52) U.S. Cl.
CPC ............ *A61K 38/57* (2013.01); *A61K 9/5068* (2013.01); *A61P 17/02* (2018.01)

(58) Field of Classification Search
None
See application file for complete search history.

(56) References Cited

U.S. PATENT DOCUMENTS

2015/0147325 A1 5/2015 Eckelman et al.

FOREIGN PATENT DOCUMENTS

WO WO-2009083880 A1 7/2009
WO WO-2023122120 A1 6/2023

OTHER PUBLICATIONS

Ain et al., Macromolecular Research (2018), 26(8), pp. 709-716.*
Inoue et al., Mediators of Inflammation (2009), vol. 2009, Article ID 101659, 7 pages.*
International Application Serial No. PCT/US2022/053560, International Search Report mailed Apr. 7, 2023, 4 pgs.
International Application Serial No. PCT/US2022/053560, Written Opinion mailed Apr. 7, 2023, 4 pgs.
Li, et al., "Recombinant fusion protein by lysozyme and antibacterial peptide enhances ischemic wound healing via angiogenesis and reduction of inflammation in diabetic db/db mice", PeerJ. vol. 9, No. e11256, (Apr. 16, 2021), 1-18.
Park, D J, et al., "Serpin-loaded extracellular vesicles promote tissue repair in a mouse model of impaired wound healing", J Nanobiotechnol. vol. 20, No. 474, (Nov. 5, 2022), 1-17.
Tao, et al., "Extracellular vesicle-mimetic nanovesicles transport LncRNA-H 19 as competing endogenous RNA for the treatment of diabetic wounds", Drug Delivery vol. 25, No. 1, (Jan. 15, 2018), 241-255.
International Application Serial No. PCT/US2022/053560, International Preliminary Report on Patentability mailed Jul. 4, 2024, 6 pgs.

* cited by examiner

*Primary Examiner* — Brian J Davis
(74) *Attorney, Agent, or Firm* — SCHWEGMAN LUNDBERG & WOESSNER, P.A.

(57) ABSTRACT

The disclosure relates to pro-reparative extracellular vesicle (EV) compositions comprising at least one fusion protein located inside the EV, the at least one fusion protein having pro-reparative biological activity. The disclosure also relates to methods of promoting wound healing in a subject suffering from at least one of obesity, diabetes, and end-stage renal failure, the method comprising administering a therapeutically effective amount of the pro-reparative EVs of any preceding claim to a wound of a subject.

19 Claims, 28 Drawing Sheets

WT EVs
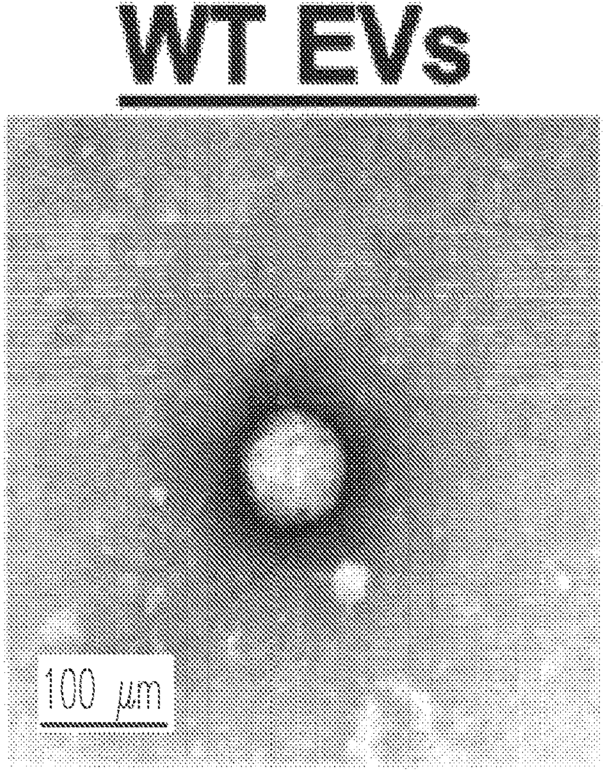
db/db EVs
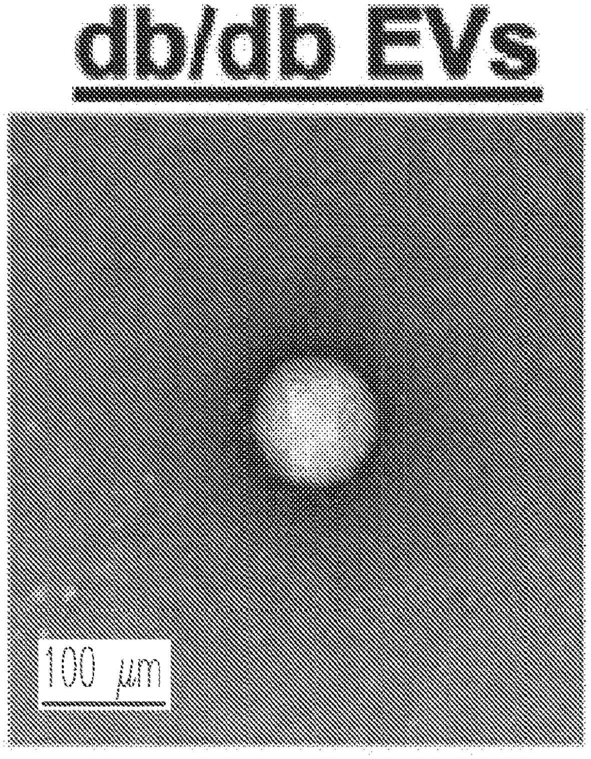
Fig. 1C

COMPOSITIONS AND METHODS FOR WOUND HEALING

This application is a U.S. National Stage Filing under 35 U.S.C. 371 from International Application No. PCT/US2022/053560, filed on Dec. 20, 2022, and published as WO 2023/122120 A1 on Jun. 29, 2023, which claims the benefit of priority under 35 U.S.C. § 119(e) to U.S. Provisional Patent Application No. 63/292,966, filed on Dec. 22, 2021, each of which is incorporated by reference herein in its entirety.

STATEMENT OF GOVERNMENT SUPPORT

This invention was made with government support under GM140137 awarded by the National Institutes of Health. The government has certain rights in the invention.

BACKGROUND

Healthy wound repair is characterized by direct and indirect intercellular interactions between cell types that mediate hemostasis, inflammation, proliferation and remodeling. Increasing evidence suggests that extracellular vesicles (EVs) mediate indirect signaling between cell types that is pro-reparative in wound healing. Studies of pathways regulating EV biogenesis have demonstrated that the cellular source of EVs affects their formation, payload, and biological activity in the wound bed. For example, platelet-derived EVs promote coagulation in hemostasis, while neutrophil-derived EVs regulate the expression of adhesion factors on the endothelium. As a wound transitions from the inflammatory phase to proliferation and re-epithelialization, macrophage-derived EVs drive macrophage polarization to an anti-inflammatory phenotype to mediate signaling between wound-edge fibroblasts and keratinocytes to promote wound closure. The resolution of the inflammatory phase of wound healing involves re-epithelialization through keratinocyte migration and remodeling of granulation tissue into more permanent extracellular matrix (ECM) through expression of collagen and proteoglycans and regulation of the secretion of proteases. In vitro studies indicate that the remodeling phase of wound healing can be stimulated by EV-mediated signaling such as in the use of mesenchymal stem cell-derived EVs that accelerate closure of chronic wounds by establishing a pro-reparative microenvironment.

Diabetes is a chronic metabolic disease that is complicated by delayed wound healing and dysregulation of the inflammatory phase wound repair, leading to chronic wounds and substantial morbidity.

SUMMARY

The instant disclosure generally relates to the identification of secreted factors in the diabetic wound bed associated with delayed cutaneous wound closure as potential therapeutic targets by using mice lacking the Leptin receptor (Lepr−/−; db/db), which is a Type II diabetic model that is hyperglycemic and presents with a well-defined phenotype of delayed cutaneous wound closure. This approach identified a signature of EVs from the wound bed of db/db mice based on their protein payload and relevance to the inflammation phase of wound healing. In one example, this approach identified several members of the Serpin family of serine protease inhibitors that are down-regulated in db/db vs. wildtype (WT) EVs, which were then re-expressed, promoted wound closure.

Serpins are of particular interest in wound healing because of their regulatory effects on specific serine proteases that are relevant in inflammation and ECM remodeling that affects cell migration and proliferation that is a hallmark of the wound response. Members of the Serpin superfamily regulate blood pressure, hormone transport, insulin sensitivity and the inflammatory response. The identification of Serpin deficiencies in diabetic wounds suggests the therapeutic potential of re-expression of these Serpins to promote tissue repair by modulating protease activity and inflammation responses. In combination with the emerging importance of EVs as therapeutic nanocarriers for proteins and nucleic acids in complex animal systems, the findings presented herein support that Serpin-loaded EVs have a therapeutic potential in promoting closure of chronic wounds.

DESCRIPTION OF THE DRAWINGS

FIG. 1G is transmission electron microscopy of WT vs. db/db EVs at 100 k magnification, size bar=100 nm. All representative images showed as observed in three independent experiments.

FIG. 2I shows representative hematoxylin and eosin staining of the injury site following treatment with WT vs. db/db EVs at 14 days (Scale bars, 0.5 mm).

DESCRIPTION

Figure 1A:
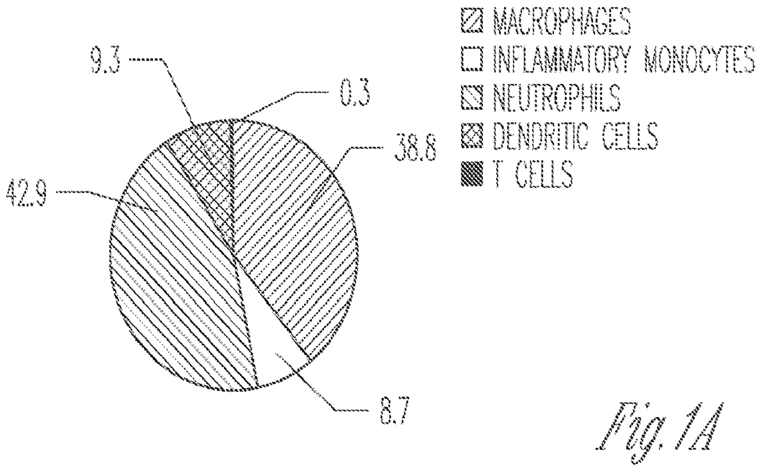
FIG. 1A shows flow cytometry analysis of cell types recruited to PVA sponges 2 days post-implantation focusing on the macrophages (orange), inflammatory monocyte (red), neutrophils; (green), dendritic cells (purple), and T cells (blue). Mean+SD, n=7.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

The disclosure generally relates to a pro-reparative extracellular vesicle (EV) composition comprising: at least one fusion protein located inside the EV, the at least one fusion protein having pro-reparative biological activity in at least one of promoting wound healing and tissue regeneration.

As used herein, the term "wound" can refer to damage or loss to any one or combination of skin layers caused by cuts, incisions (including surgical incisions), abrasions, microbial infections, diseases or disorders, necrotic lesions, lacerations, fractures, contusions, burns, and amputations. Non-limiting examples of wounds can include bed sores, thin dermis, bullous skin disease, and other cutaneous pathologies, such as subcutaneous exposed wounds that extend below the skin into the subcutaneous tissue. In some instances, a subcutaneous exposed wound may not affect underlying bones or organs.

As used herein, the term "pro-reparative" generally means that the compositions described herein promote at least one of wound healing and tissue regeneration near and/or in a wound of a subject (e.g. a subject whose wounds are chronic) within 14 days or less (e.g., 13 days or less, 12 days or less, 11 days or less, 10 days or less, 5 days or less, 2 days or less; within about 5 days to about 10 days). For example, the compositions described herein promote at least 25%, 30%, 40%, 50%, 60%, 70% or at least 80% of at least one of wound healing and tissue regeneration in a subject within 14 days or less (e.g., 13 days or less, 12 days or less, 11 days or less, 10 days or less, 5 days or less, 2 days or less; within about 5 days to about 10 days). The term "chronic wound" as used herein refers to wounds that take a long time (e.g., about 14 days) to heal or that do not heal without external intervention (e.g., within about 14 days). Yet further, as used herein, a "chronic wound," also referred to as "chronic ulcer" can be broadly classified into three major types: diabetic ulcers, venous stasis ulcers, decubitus or pressure ulcers. Still further, a chronic wound can also include infected wounds that take a long time to heal.

The fusion protein contained in the EV of the disclosure can be any suitable fusion protein so long as it has pro-reparative biological activity in wound healing and tissue regeneration. In one example, the protein comprised in the fusion protein is downregulated or otherwise dysregulated in diabetic wounds or other models of impaired wound healing (e.g., models related to ischemia, obesity, infection, and aging). In another example, the protein comprised in the fusion protein regulates proteases relevant in inflammation. Thus, for example, the protein comprised in the fusion protein inhibits proteases relevant in inflammation. In another example, the protein activates proteases relevant in inflammation. The at least one fusion protein may comprise, in one example, a serine protease inhibitor. The at least one fusion protein may comprise, in one example, a serine protease activator. In one example, the at least one fusion protein is myristoylated. In one example, the protein comprised in the myristoylated protein is substantially or completely absent in extracellular vesicles of a subject suffering from at least one of obesity, diabetes, and end-stage renal failure. While not wishing to be bound by any specific theory, it is believed that myristoylation can, among other things, promote anchoring of the fusion protein to the membrane, such that the fusion protein may be loaded/trafficked/shuttled/anchored (e.g., anchored to an EV membrane) into the EVs described herein. But it should be understood that the at least one fusion protein can comprise other modifications that allow it to otherwise be loaded/trafficked/shuttled/anchored (e.g., anchored to an EV membrane) into the EVs described herein.

The at least one fusion protein can comprise a serine protease inhibitor, for example, such as serine protease inhibitors from the serpin family of serine protease inhibitors. Examples of serine protease inhibitors from the serpin family of serine protease inhibitors include, but are not limited to, at least one of serpin A1, serpin F2, and serpin G1.

The EVs comprised in the pro-reparative EV compositions comprised herein may be generated by various methods (e.g., in vivo, using the methods described herein, or synthetically) and may have various morphologies. For example, they may comprise either one lipid bilayer (unilamellar vesicle) or a series of concentric bilayers separated by narrow aqueous compartments (multi-lamellar vesicle or MLV). Engineered vesicles are also contemplated herein. In some examples, the EVs contemplated herein are substantially homogeneous in size and density distribution. For example, the EVs used herein have a diameter (mean particle diameter) from about 15 to about 500 nm, about 50 nm and about 250 nm, 80 nm and about 100 nm, or about 80 nm and about 100 nm; about 300 nm or less, 250 nm or less, 200 nm or less, 150 nm or less, 100 nm or less, or 50 nm or less. For example, the pro-reparative EV compositions described herein can comprise a population of EVs that is enriched in EVs having a size ranging between about 80 nm and about 100 nm. The size of the EVs contemplated herein can be determined by any suitable method known in the art including single particle optical sizing (SPOS), scanning electron microscopy, light scattering, laser diffraction, coulter counter (electrical zone sensing), and digital image analysis. EVs of a desired size can be isolated using methods known in the art including size exclusion chromatography and density gradient centrifugation.

The disclosure is also directed to kits. Kits may be conveniently assembled for use with the EVs and pro-reparative compositions described herein. The kit can contain at least one container containing one or more of the components of the compositions described herein. Moreover, kits can include standard reagents and/or pre-measured components. Such kits can include, for example, buffers. Finally, the kits can further include instructions regarding how the kit is to be used. In one example, a kit comprises at least two or at least three of the compounds described herein, each compound in a suitable container.

The disclosure also includes a method of promoting wound healing in a subject suffering from at least one of obesity, diabetes, and end-stage renal failure, the method comprising administering a therapeutically effective amount of the pro-reparative EVs described herein to a wound of a subject. The wound can be, for example, a chronic wound. The pro-reparative EVs can accelerate closure of a chronic wound. For example, the pro-reparative EVs can accelerate closure of a chronic wound in a subject within 14 days or less (e.g., 13 days or less, 12 days or less, 11 days or less, 10 days or less, 5 days or less, 2 days or less; within about 5 days to about 10 days). For example, the compositions described herein promote at least 25%, 30%, 40%, 50%, 60%, 70% or at least 80% of at least one of wound healing and tissue regeneration in a subject within 14 days or less (e.g., 13 days or less, 12 days or less, 11 days or less, 10 days or less, 5 days or less, 2 days or less; within about 5 days to about 10 days).

Figure 6:
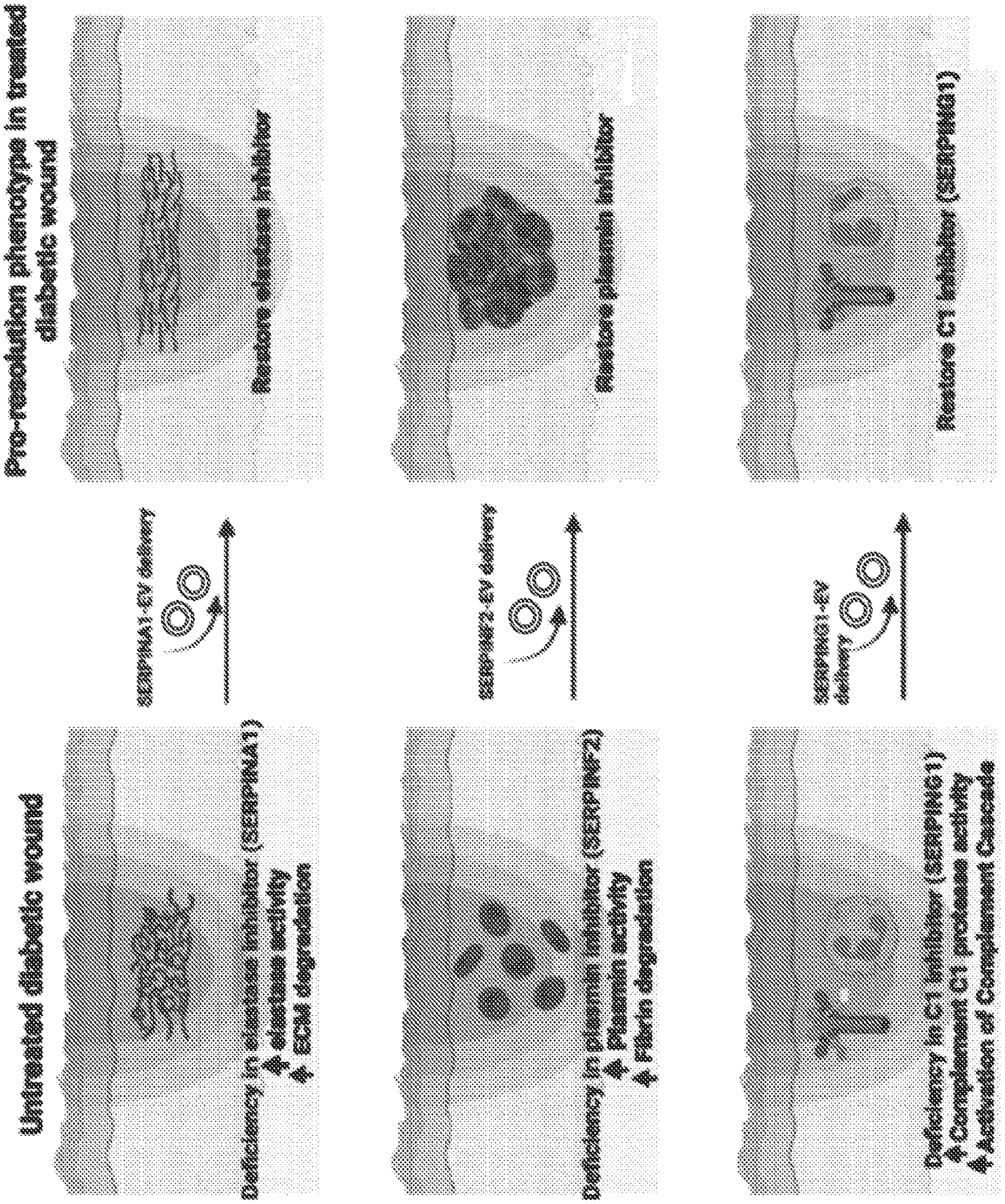
FIG. 6 is a model for serpin-loaded EV action in accelerating a pro-resolution phenotype. (Top) In diabetic wounds, it is proposed that increased elastase activity increases degradation of the extracellular matrix (ECM) that can be reversed by delivery of SERPINA1-EVs to promote healthy ECM. (Middle) Decreases in plasmin inhibitor of diabetic wounds increases plasmin activity and degradation of fibrin that can be reversed by delivery of SERPINF2-EVs leading to formation of a beneficial fibrin scaffold. (Bottom) The loss of the inhibitor of the Complement C1 protease activity (C1) in diabetic mice that increases production of complement cascade products, which can be reversed by delivery of SERPING1-EVs that suppress the activation of complement cascade, activation of neutrophils, and promotes the resolution of the inflammation phase of wound repair. Created with Biorender.com.

The disclosure also relates to a method of reversing the inhibitory activity of at least one of elastase, plasmin, and complement (e.g., complement factors, such as complement C1 as shown in FIG. 6 herein) in a subject suffering from (or having been diagnosed with) at least one of obesity, diabetes, and end-stage renal failure, the method comprising administering a therapeutically effective amount of the pro-reparative EVs described herein. The elastase, plasmin, and complement activity may be near or on/in a wound (e.g., a chronic wound).

Techniques and dosages for administration of the fusion constructs described herein may vary depending on the type of protein used. Regulatory agencies may require that the EVs comprising the fusion constructs described herein be formulated so as to have acceptably low levels of pyrogens. Accordingly, therapeutic compositions/formulations may generally be distinguished from other formulations in that they may be substantially pyrogen free, or at least contain no more than acceptable levels of pyrogen as determined by the appropriate regulatory agency (e.g., the U.S. Food and Drug Administration).

In some embodiments, the EVs comprising the fusion constructs described herein are pharmaceutically acceptable to a mammal, in particular a human. A "pharmaceutically acceptable" EV and/or fusion construct refers to an EV and/or fusion construct that is administered to an animal without significant adverse medical consequences.

Therapeutic compositions may be administered with a pharmaceutically acceptable diluent, carrier, or excipient, in unit dosage form. Administration may be parenteral (e.g., subcutaneous) or topical, as non-limiting examples. The composition can be in the form of a liquid, a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

A therapeutically effective dose refers to a dose that produces the therapeutic effects for which it is administered. The exact dose will depend on the disorder to be treated, and may be ascertained by one skilled in the art using known techniques. In general, the EVs comprising the fusion constructs described herein are administered at about 0.01 μg/kg to about 50 mg/kg per day, preferably 0.01 mg/kg to about 30 mg/kg per day, most preferably 0.1 mg/kg to about 20 mg/kg per day. The EVs comprising the fusion constructs described herein may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

As used herein, the terms "treatment" and "treating" can refer to obtaining a desired physiologic, dermatological, or cosmetic effect by the present invention. The effect may be prophylactic in terms of completely or partially preventing a disease, disorder, or symptom thereof and/or may be therapeutic in terms of a partial or complete cure for a disease, disorder, and/or symptom attributable to the disease or disorder. Thus, the terms can cover any treatment of a disorder or disease in a subject, such as: (a) preventing a wound from occurring in a subject that may be predisposed to developing the wound but has not yet been diagnosed as having it; (b) inhibiting a wound, e.g., arresting its development; and (c) relieving, alleviating, or ameliorating a wound by, for example, causing regression of the wound.

As used herein, the term "cosmetic effect" can refer to any treatment using the EVs comprising the fusion constructs described herein that preserves, restores, bestows, simulates, or enhances the appearance of bodily beauty or appears to enhance the beauty or youthfulness, specifically as it relates to the appearance of tissue or skin.

As used herein, the terms "healing" and "heal" can refer to improving the natural cellular processes and humoral substances of tissue repair such that healing is faster, and/or the resulting healed area has less scaring, and/or the wounded area possesses tissue strength that is closer to that of uninjured tissue, and/or the wounded tissue attains some degree of functional recovery. The terms can additionally or alternatively refer to the physiological process wherein a wounded area returns to an effectively normal state. When the wound is an open wound, for example, healing can refer to the process whereby the skin or mucosa re-forms a continuous barrier. The skilled artisan will appreciate that, after healing, the area of the wound may comprise scar tissue that is not identical to the surrounding tissue.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substantially no" as used herein refers to less than about 30%, 25%, 20%, 15%, 10%, 5%, 3%, 2%, 1%, 0.5%, 0.1%, 0.05%, 0.001%, or at less than about 0.0005% or less or about 0% or 0%.

Those skilled in the art will appreciate that many modifications to the embodiments described herein are possible without departing from the spirit and scope of the present disclosure. Thus, the description is not intended and should not be construed to be limited to the examples given but should be granted the full breadth of protection afforded by the appended claims and equivalents thereto. In addition, it is possible to use some of the features of the present disclosure without the corresponding use of other features. Accordingly, the foregoing description of or illustrative embodiments is provided for the purpose of illustrating the principles of the present disclosure and not in limitation thereof and can include modification thereto and permutations thereof.

EXAMPLES

The disclosure can be better understood by reference to the following examples which are offered by way of illustration. The disclosure is not limited to the examples given herein.

Figure 1B:
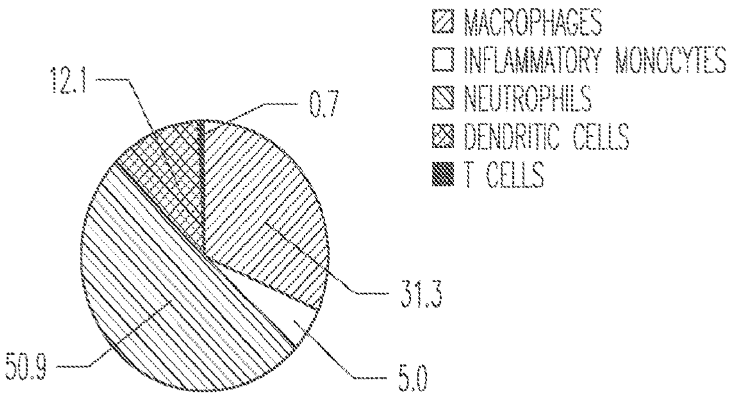
FIG. 1B shows mean cell type distributions in the PVA sponges 7 days post-implantation. Mean+SD, n=4 independent experiments, t-test comparison test.
Figure 1C:
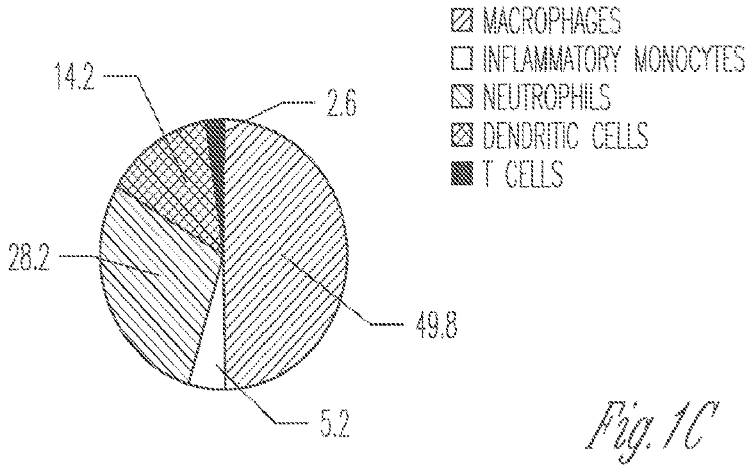
FIG. 1C shows mean cell type distribution of cell types in PVA sponges 14 days post-implantation. Mean+SD, n=10 independent experiments, t-test comparison test.
Figure 1D:
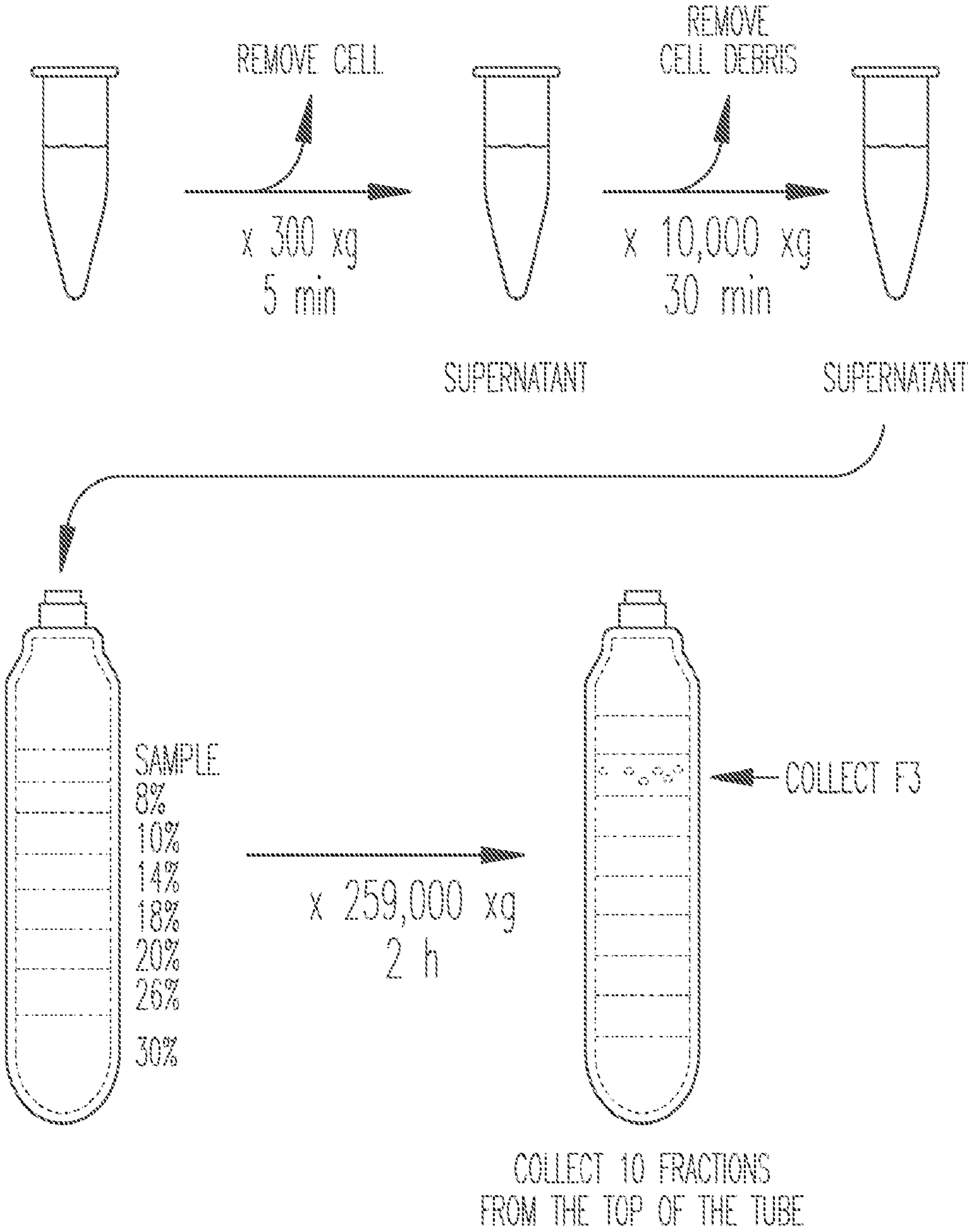
FIG. 1D shows a schematic of EV isolation workflow based on density gradient ultracentrifugation.
Figures 1, 1E:
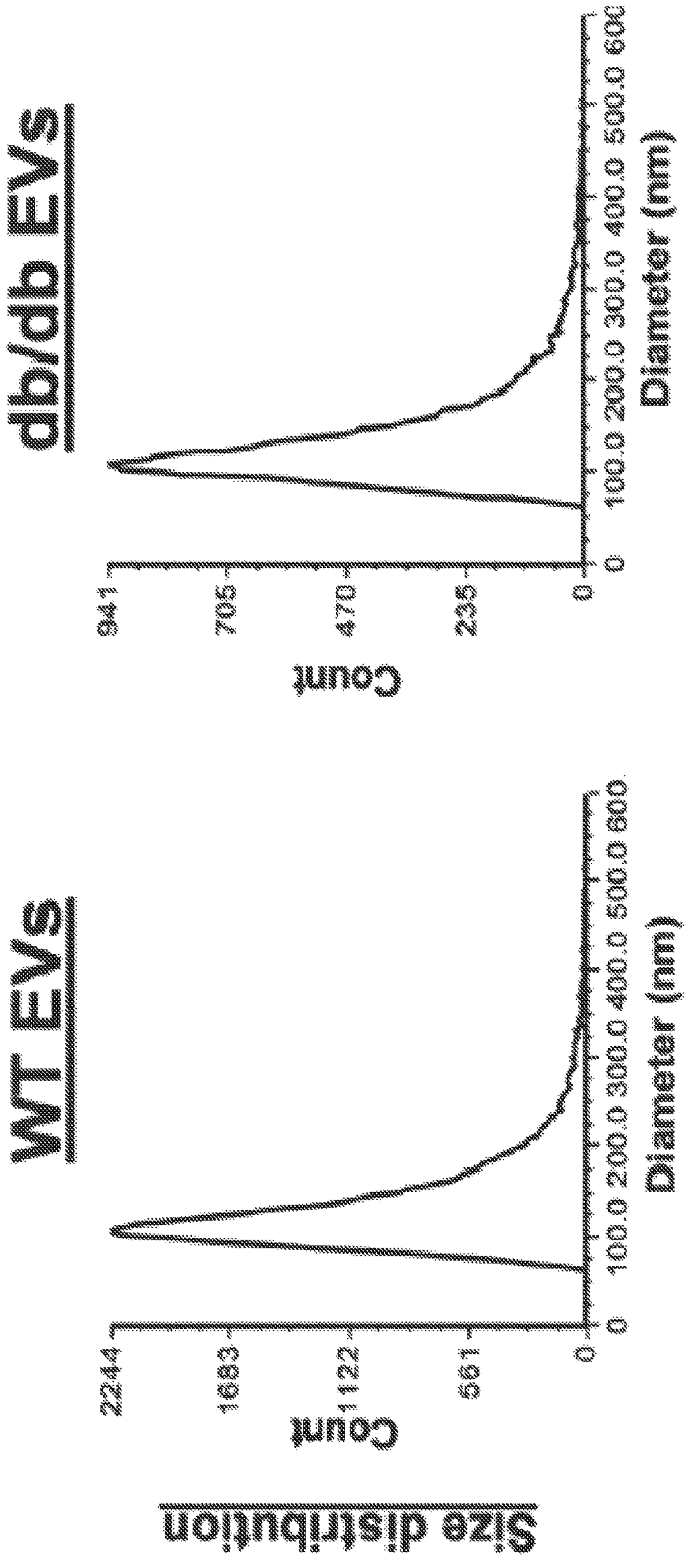
FIG. 1E shows a representative example of the validation studies defining size distribution and light scatter on WT and db/db EVs by vFRed analysis.

Subcutaneous Sponge Implants as an In Vivo Source of EVs for Allotransplantation Implants of sterile polyvinyl alcohol (PVA) sponge elicited the recruitment of neutrophils and macrophages relevant in the inflammatory phase of wound healing, therefore, wound fluid from these implants were analyzed for cellular and EV content (FIG. 1). Immunophenotyping by flow cytometry of wound fluid cells collected over a time course of 2-14 days identified an infiltration of leukocytes such as macrophages ($CD45^+$, $CD11b^+$, $F4/80^+$), inflammatory monocytes ($CD45^+$, $Ly6c^+$, $CD11b^+$), dendritic cells (DCs, $CD45^+$, $CD11c^+$, $MHCII^+$, $CD11b^+$), neutrophils ($CD45^+$, $Ly6G^{high}$, $Ly6c^{int}$), and T cells ($CD4^+$). Neutrophils and macrophages predominated at each time point (FIG. 1A-C) followed by DCs, inflammatory monocytes and T cells. In combination with Supplementary Data showing statistical analysis, expression of canonical EV biogenesis genes and cell profiling of WT vs. db/db mice, these studies defined the immune cell phenotype of the implant model used as an in vivo EV source relevant to the inflammatory phase of wound healing. To characterize the EV released in the PVA sponge model, EVs were enriched by density ultracentrifugation (FIG. 1D) and analyzed by vesicle flow cytometry to demonstrate a similar EV size distribution (FIG. 1E), concentration, expression of canonical EV markers (FIG. 1F), and appearance by transmission electron microscopy (FIG. 1G) in WT and db/db EVs that was supported by vesicle flow cytometry (vFC) analysis based on MISEV2018 standards. Quantitative analysis of WT and db/db EVs using vFC demonstrates consistency in EV size and light scatter. Similarly, EVs from WT and db/db mice were comparable for their staining for EV membrane phosphatidylserine using Annexin V and expression of the tetraspanins CD9, CD63 and CD81 (TS) on the EV surface with normalized expression of Annexin-V and TS expressed as histograms). Together, these representative plots demonstrate the analytical power of vFC for quantitative analysis of complex EV mixtures from biological fluids such as the PVA sponge and wound fluid.

PRO-Reparative Capacity of EVs Defined by Genetics of Donor

Figures 1, 1E, 2:
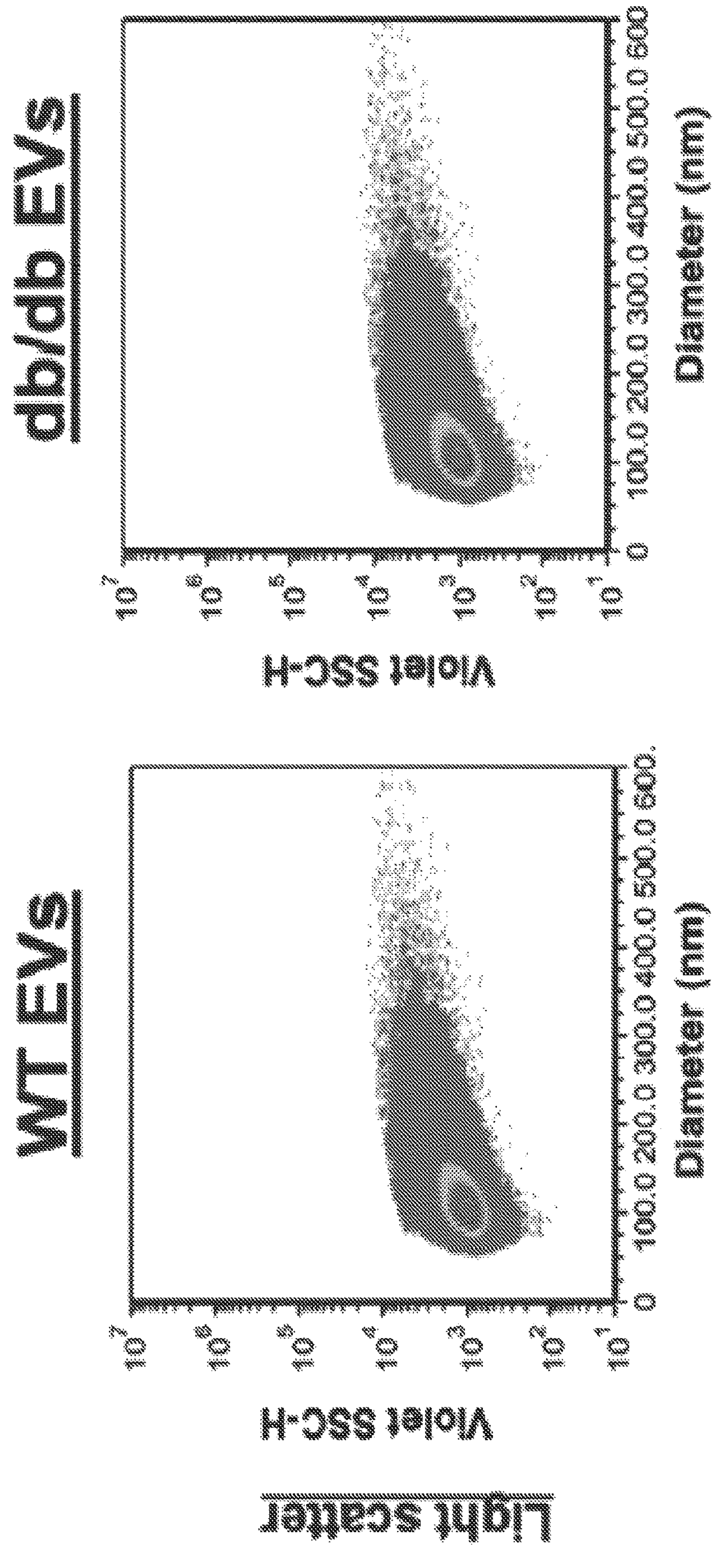
Figure 1F:
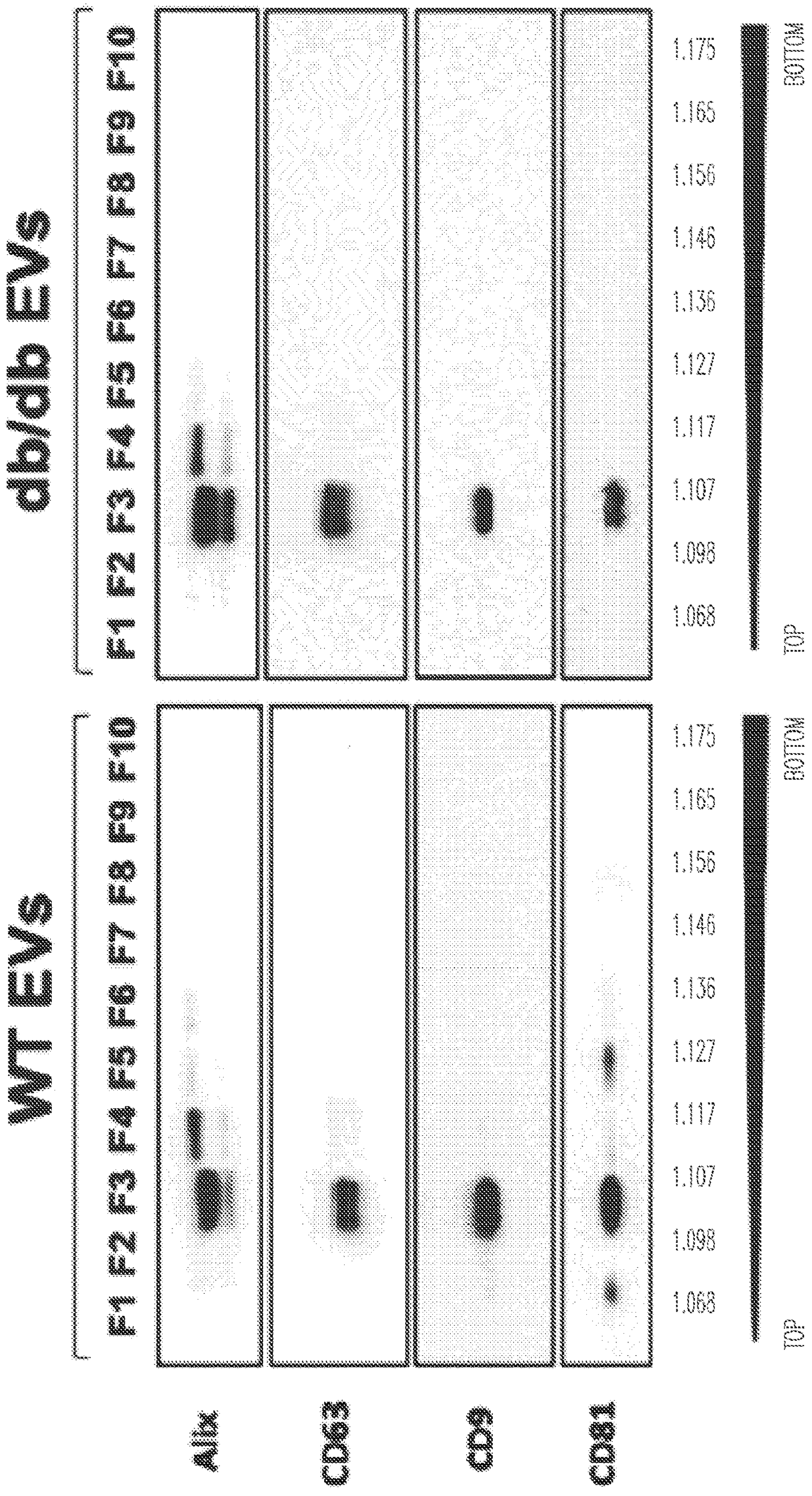
FIG. 1F is an immunoblot showing the specific EV markers (CD81, CD9, CD63, and Alix) in the density gradient fractions on the WT vs. db/db EVs. n=6 independent experiments.
Figure 2A:
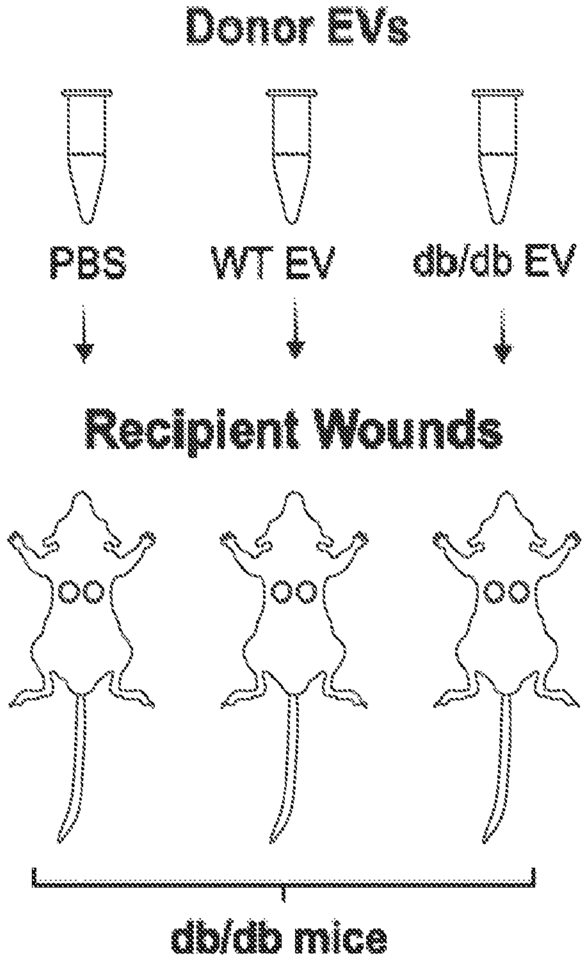
FIG. 2A is a schematic of EV collection from sponge implants implanted in WT and db/db mice (i.e. Donor) followed by adoptive transfer to full thickness wounds into db/db mice (i.e. Recipient).
Figure 2B:
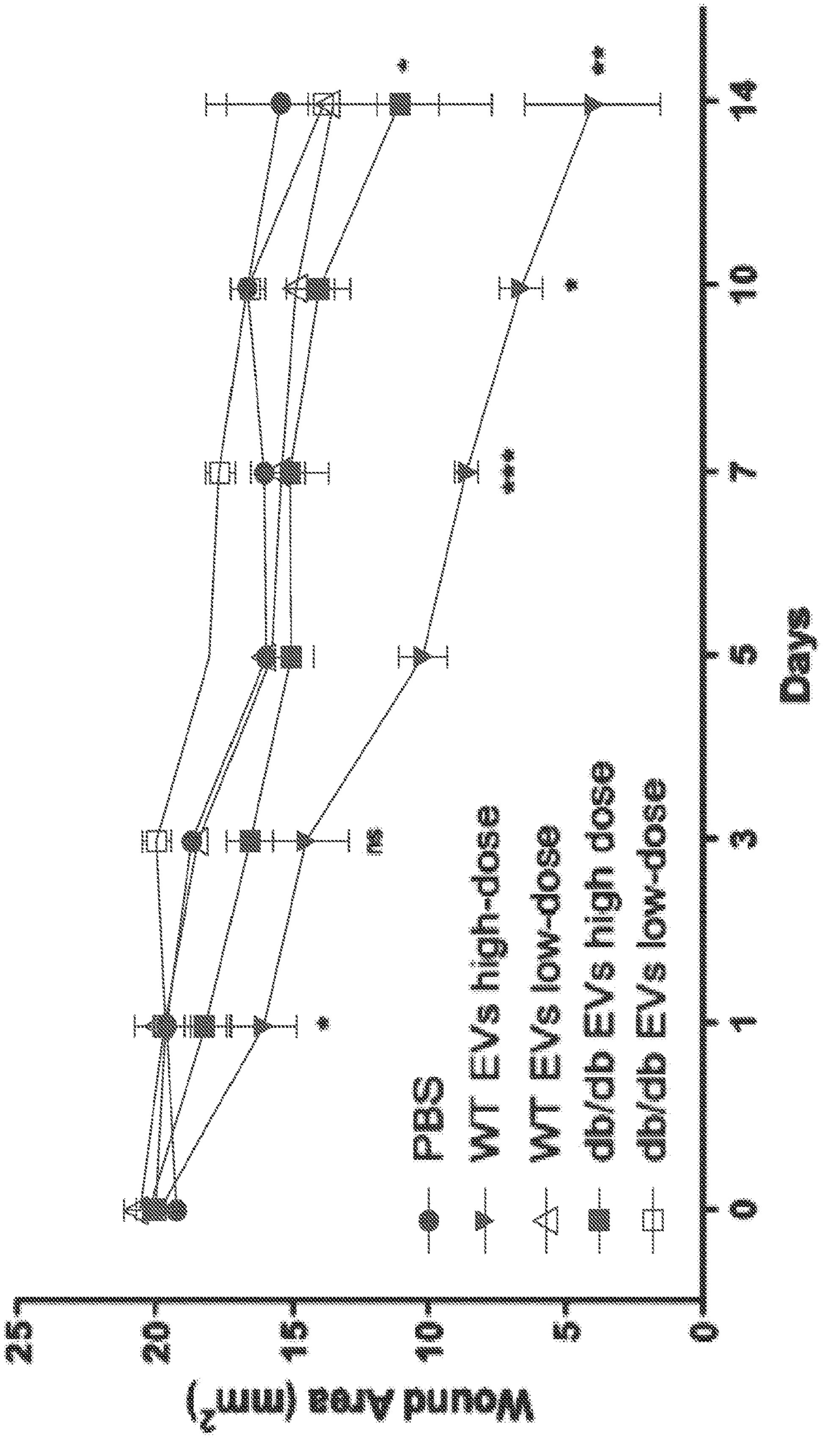
FIG. 2B shows kinetics of wound closure area following treatment with EVs enriched WT vs. db/db donor mice (2-way ANOVA of WT vs db/db high dose EV treated mice, $p$-value<0.0001).
Figure 2C:
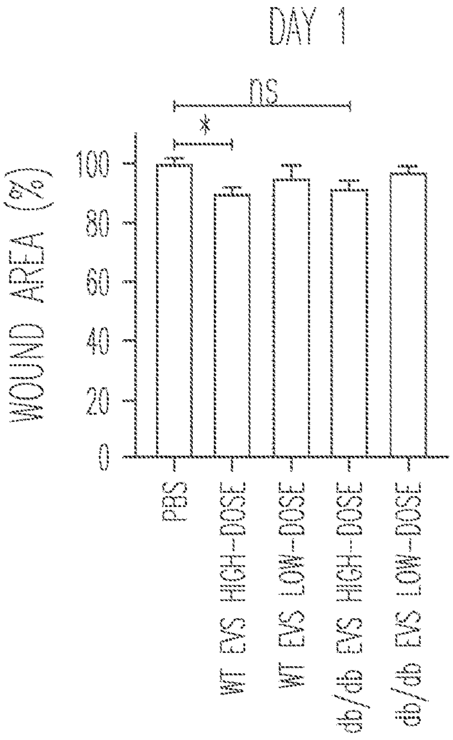
FIG. 2C shows additional statistical analysis of wound closure efficiency is shown on Day 1 (Means+SD, p-value: *<0.001, <0.005, *<0.05).
Figure 2D:
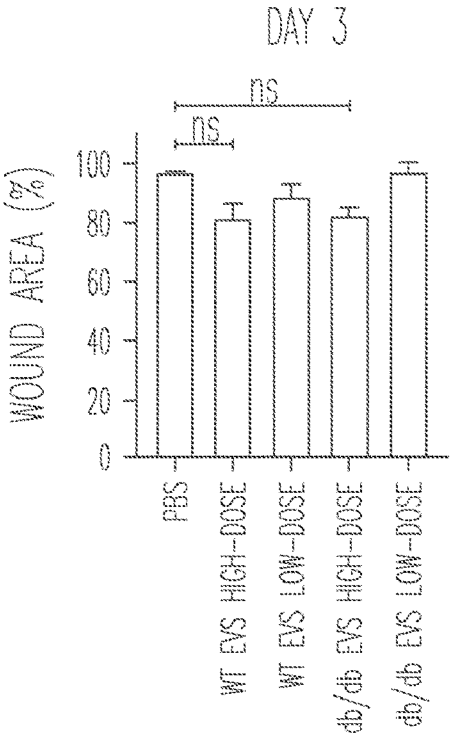
FIG. 2D shows additional statistical analysis of wound closure efficiency is shown on Day 3 (Means+SD, p-value: *<0.001, <0.005, *<0.05).
Figure 2E:
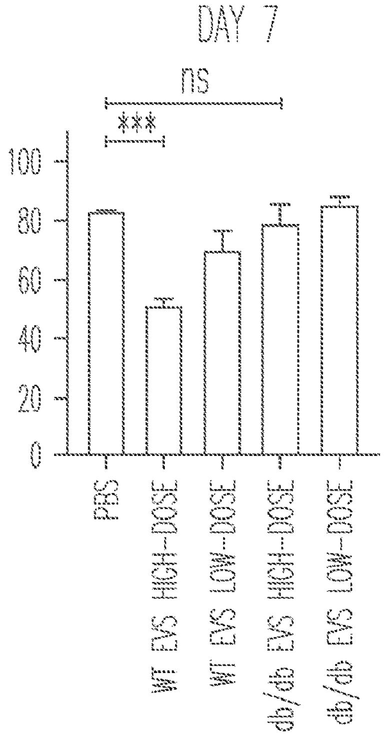
FIG. 2E shows additional statistical analysis of wound closure efficiency is shown on Day 7 (Means+SD, p-value: *<0.001, <0.005, *<0.05).
Figure 2F:
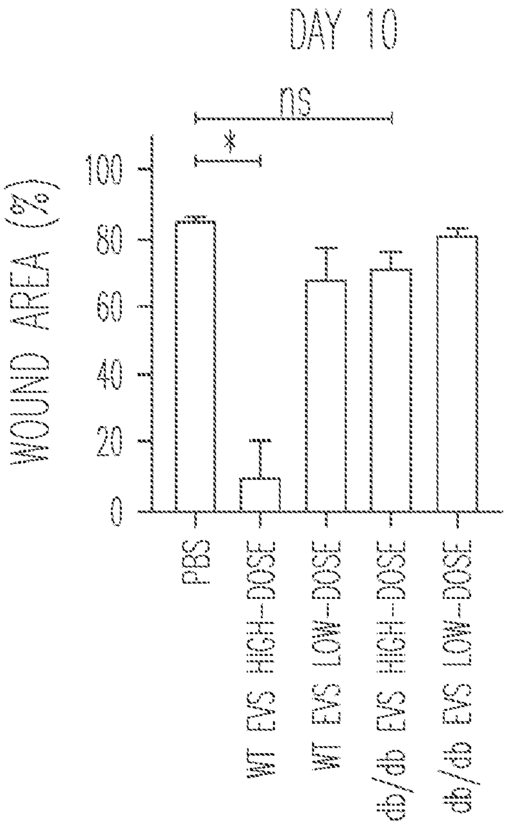
FIG. 2F shows additional statistical analysis of wound closure efficiency is shown on Day 10 (Means+SD, p-value: *<0.001, <0.005, *<0.05).
Figure 2G:
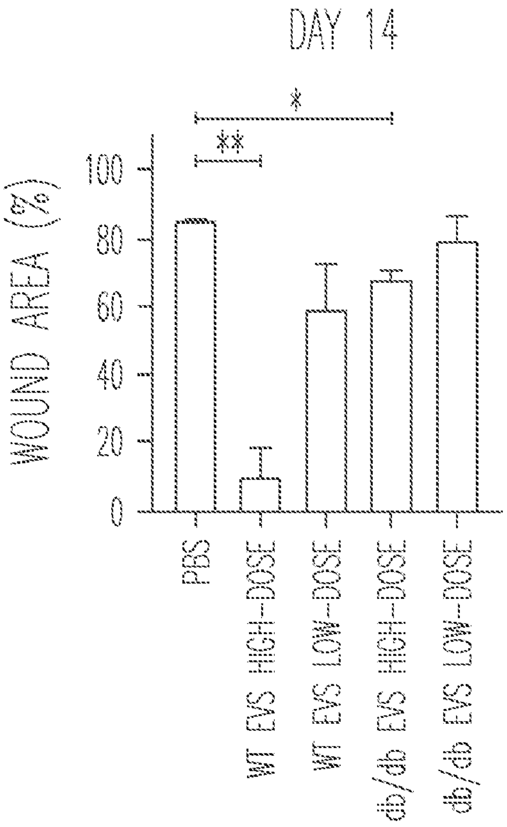
FIG. 2G shows additional statistical analysis of wound closure efficiency is shown on Day 14 (Means+SD, p-value: *<0.001, <0.005, *<0.05).
Figure 2H:
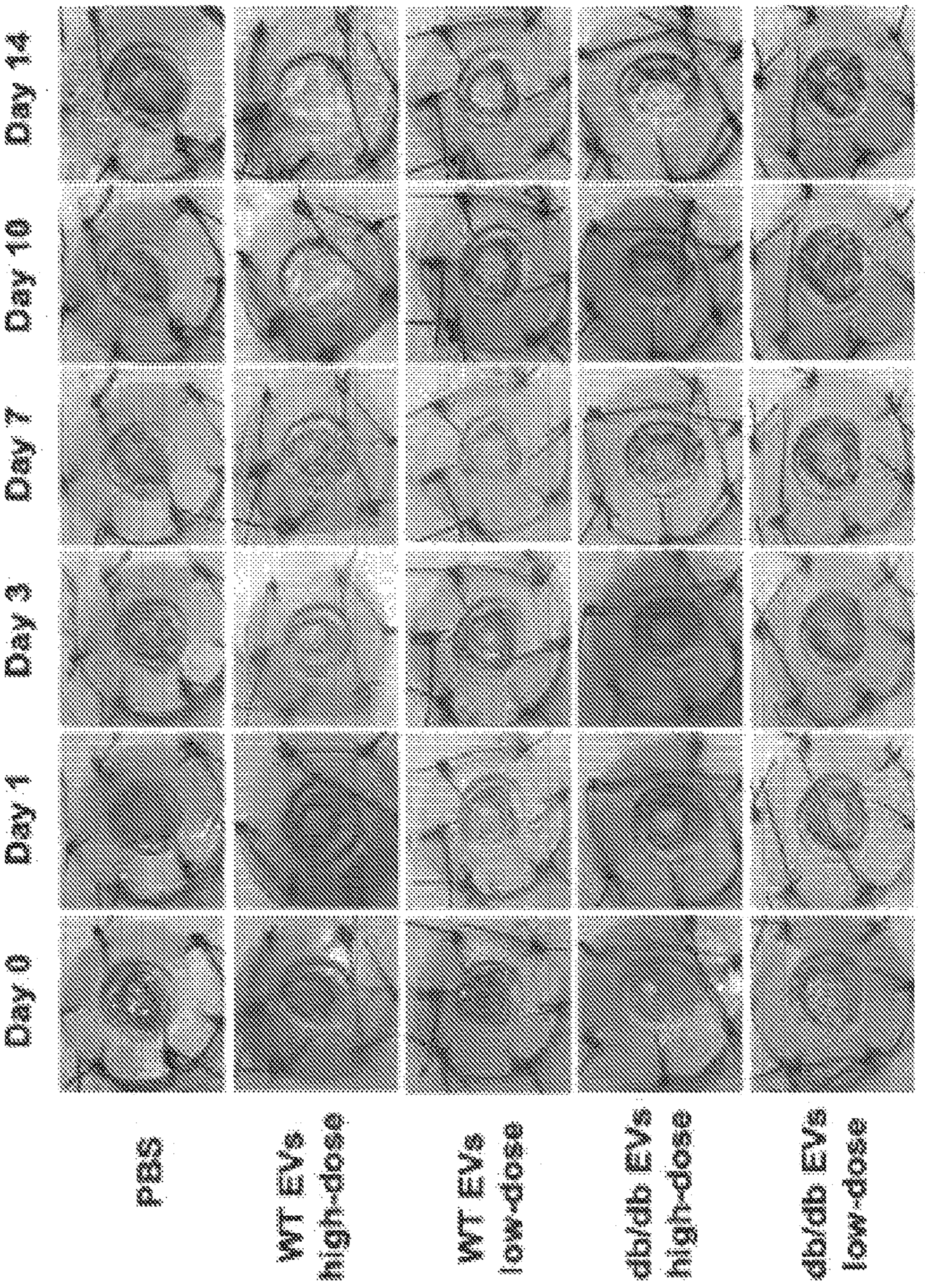
FIG. 2H shows representative images of splinted wounds treated with EVs.
Figure 21:
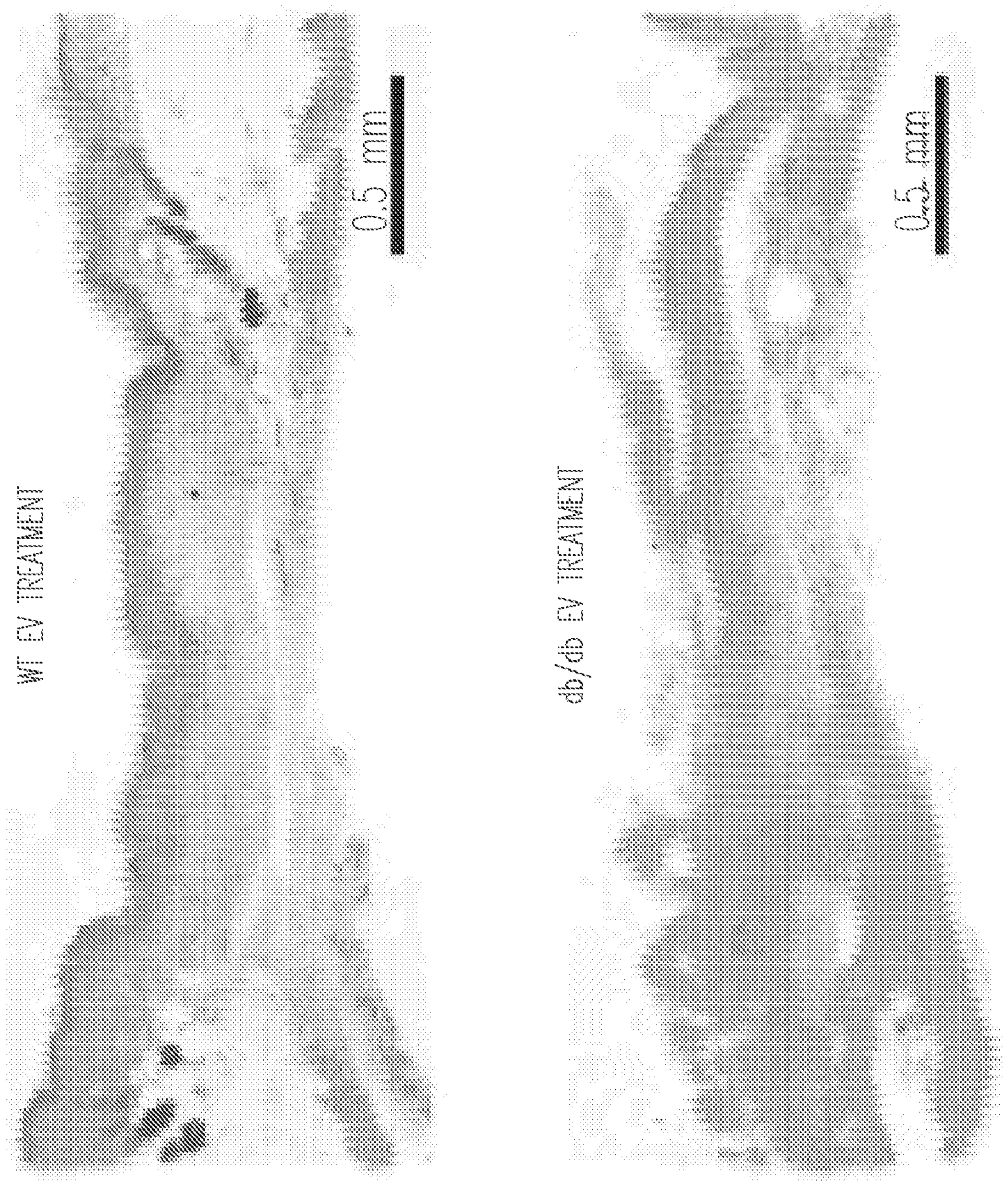

To determine whether there were differences in the biological activity of WT vs. db/db EVs, EVs from PVA sponges implanted in WT or db/db mice were enriched, and adoptively transferred them into a full thickness cutaneous wound made in the dorsum of recipient db/db mice. EVs from each donor mouse genotype were administered once in either of two doses onto the wound sites of naïve db/db mice (FIG. 2A). Treatment of db/db wounds with donor EVs led to a dose-dependent acceleration of wound closure with WT EVs that contrasted with db/db EVs at the high EV dose ($7.5\times10^5$ particles/μL) (FIG. 2B). Statistically significant db/db-mediated uncoupling of the pro-reparative activity of EVs was observed at days 7-14 (FIGS. 2C-G). Representative images of replicates (n=4 at each time point for each condition) show delayed wound closure in db/db-treated EVs at the high dose ($7\times10^5$ particles/μL) (FIG. 2H) compared to treatment with WT EVs that was consistent with a delay in re-epithelialization of wounds treated with db/db EVs at day 14 (FIG. 2I, right).

Identification of Changes in EV Protein Payloads Based on Mass Spectrometry

Figure 3A:
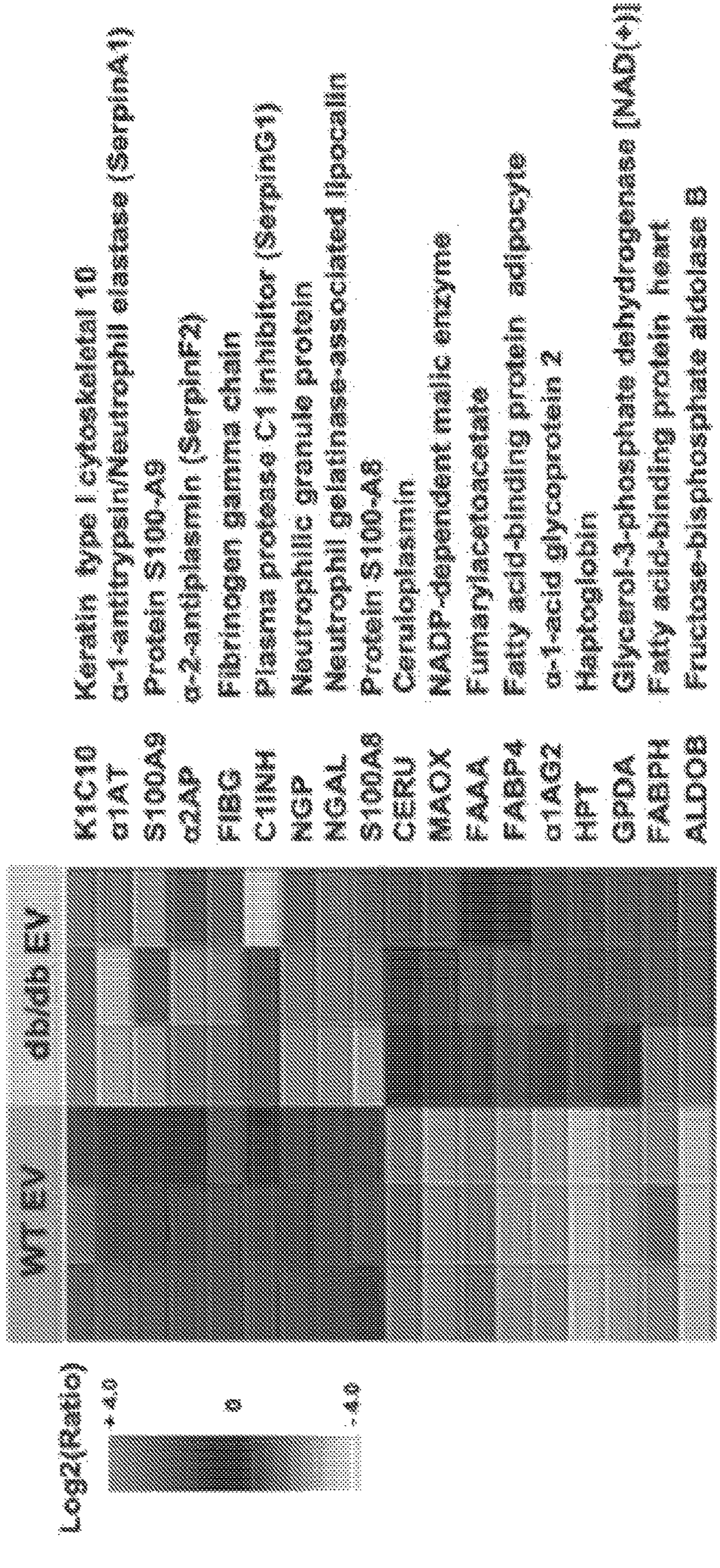
FIG. 3A is a heatmap of protein expression in WT and db/db EVs showing protein levels elevated in WT EVs compared to db/db EVs, and protein levels in WT EVs that are lower than db/db EVs. n=3 independent animals of each genotype.
Figure 3B:
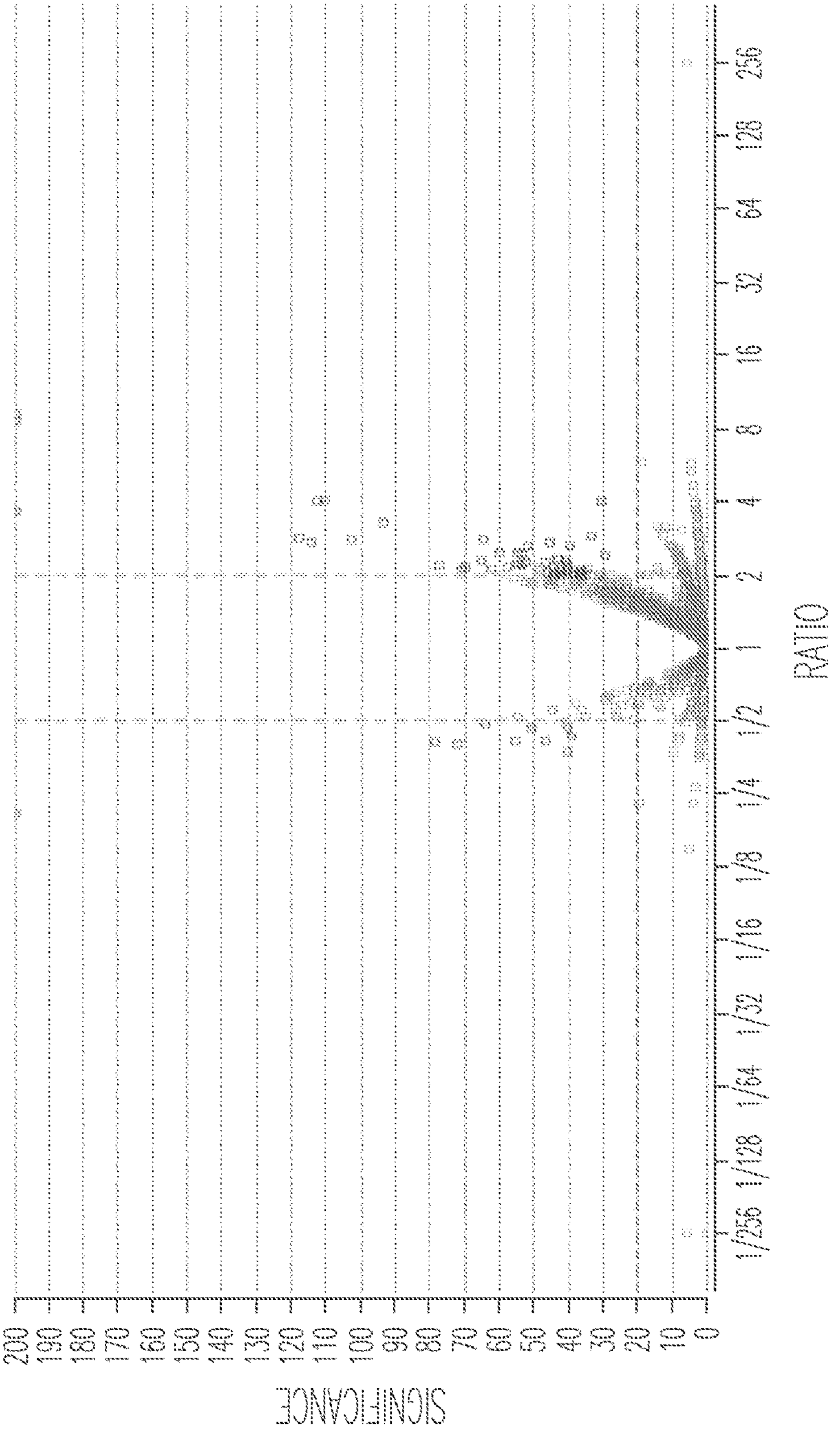
FIG. 3B is a volcano plot showing that the standard deviation of EV proteins identified and magnitude of fold-changes that support the high statistical significance of EV proteins identified. n=3 biological replicates for each genotype.
Figure 3C:
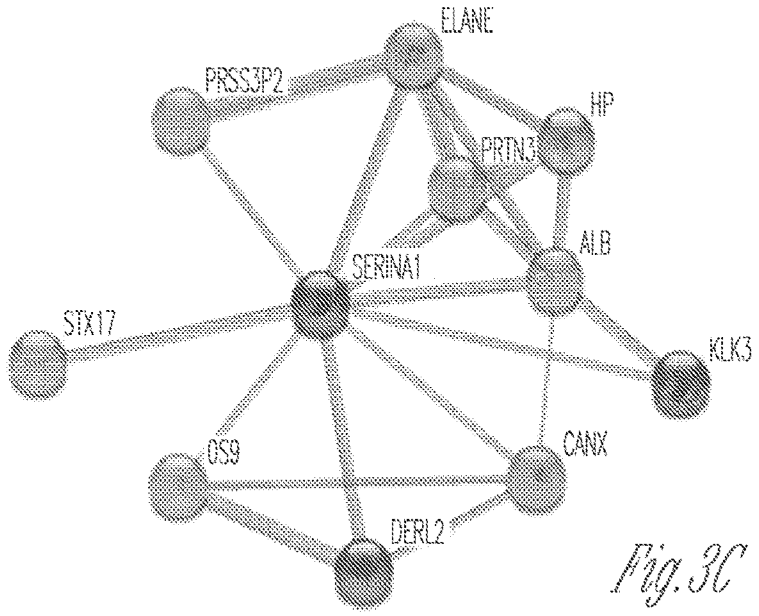
FIGS. 3C-3E are string analyses of predicted proteins that may interact with SERPINA1, SERPINF2, and SERPING1. All representative images showed as observed in three independent experiments.
Figure 3D:
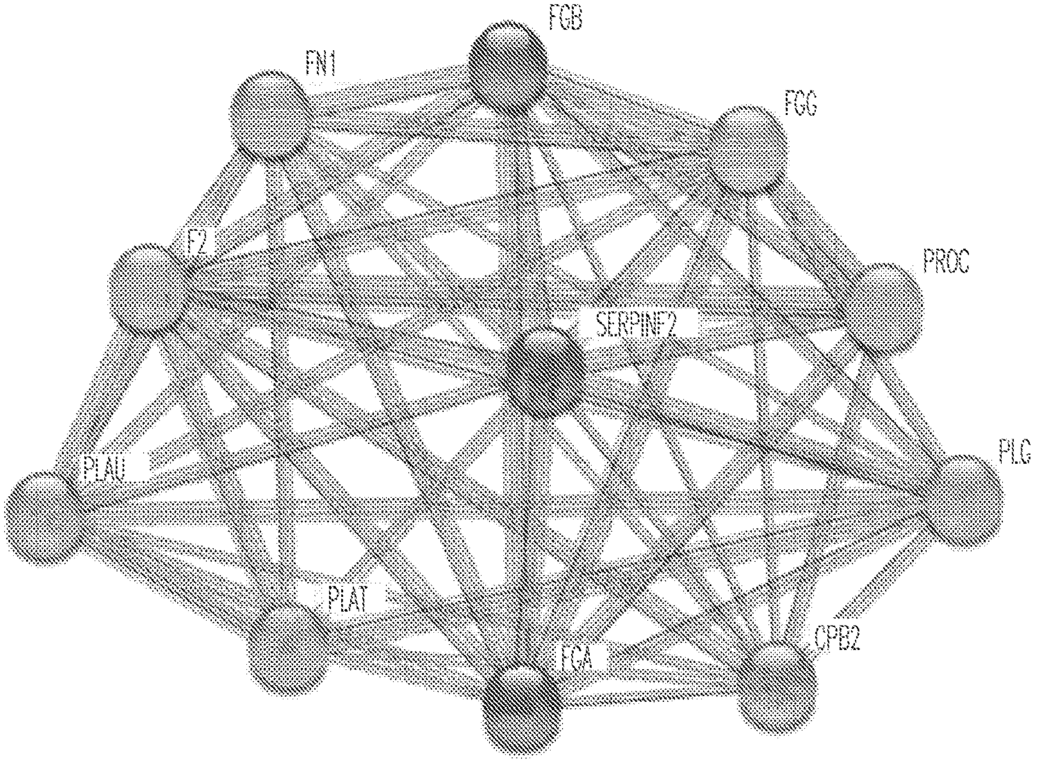
Figure 3E:
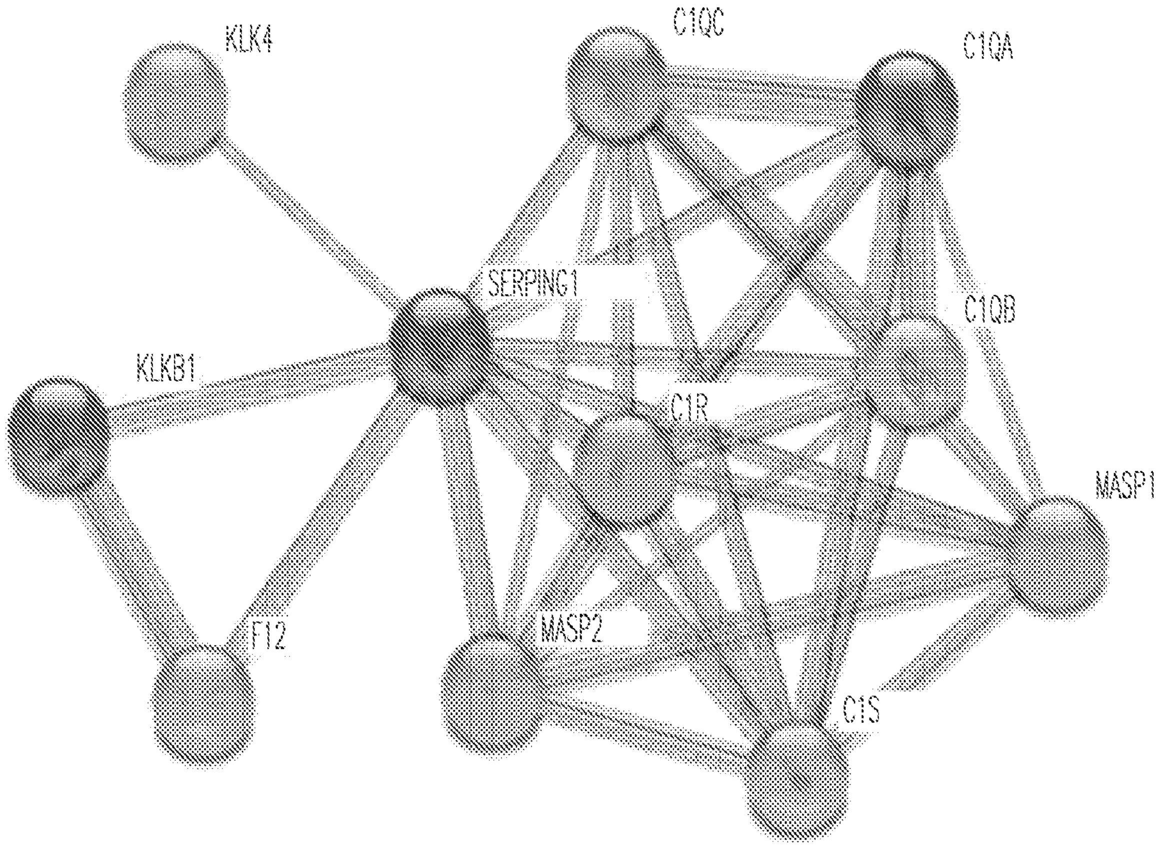

Based on differences in biological activity between db/db and WT EVs in promoting wound closure, EVs from the db/db vs. WT donors were subjected to mass spectrometry to measure changes in EV proteins that could account for differences in their biological activity. 5,315 proteins were identified that were differentially expressed in db/db vs. WT EVs, with a heat map showing changes in protein expression in biological replicates (n=3 for each genotype) that were most highly down-regulated in db/db EVs (FIG. 3A, top) and proteins that were up-regulated in db/db EVs compared to WT EVs (FIG. 3A, bottom). Among the proteins that were down-regulated in the db/db EVs, three protease inhibitors α-1-antitrypsin 1 (α1AT), α-2-antiplasmin (α2AP), and plasma protease C1 inhibitor (C1INH) were identified as part of the Serpin family of Serine protease inhibitors and suggested their potential relevance in wound bed hemostasis, fibrinolysis, and inflammation. Additional factors relevant in neutrophil activation such as neutrophilic granule protein and neutrophil gelatinase-associated lipocalin were also decreased in db/db EVs. Of the proteins that were up regulated in db/db EVs, several proteins associated with metabolism were identified, consistent with the hypermetabolic phenotype of db/db mice. These proteomic analyses demonstrated that the EVs released in WT vs. db/db donor could be distinguished on the basis of the expression of protease inhibitors, neutrophil activation and metabolic enzymes. With a focus on examining a class of regulatory molecules relevant to the extracellular matrix, cell migration and re-epithelialization of the wound bed. A String analysis revealed linkages between SerpinA1 with STX17, KLK3 and OS9 (FIG. 3C), SerpinF2 with CPB2 and FGB (FIG. 3D), and SerpinG1 with KLK4, KLKB1, and C1R (FIG. 3E). Based on the relevance of Serpin activity in the wound bed, and EVs as nanocarriers of functional payloads, the potential for over-expressing proteins identified as being down-regulated in a proteomics screen were examined to then test their biological activity in keratinocyte migration and wound healing.

Design and Activity Analysis of Serpin-Loaded EVs in Wound Healing

Figure 4A:
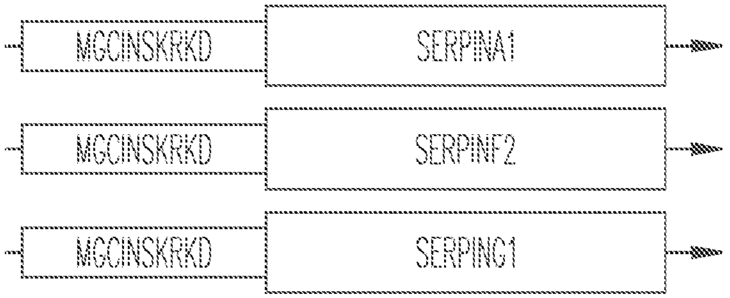
FIG. 4A shows fusions of an amino terminal myristoylation sequence with each Serpin were cloned into lentiviral vectors.
Figure 4D:
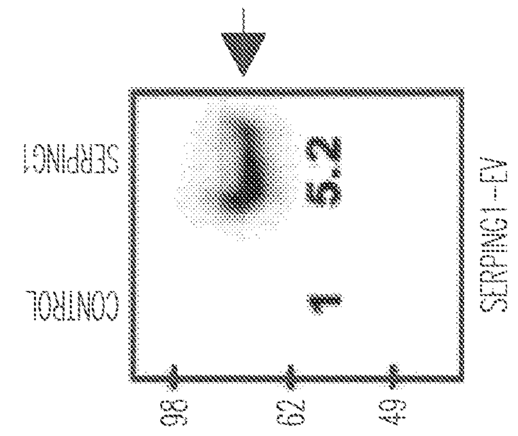
FIGS. 4B-D show validation of three Serpin-loaded EVs by immunoblotting in cultured media. Sham is PBS and Empty is the empty vector used for the myristoylation fusions.
Figure 4C:
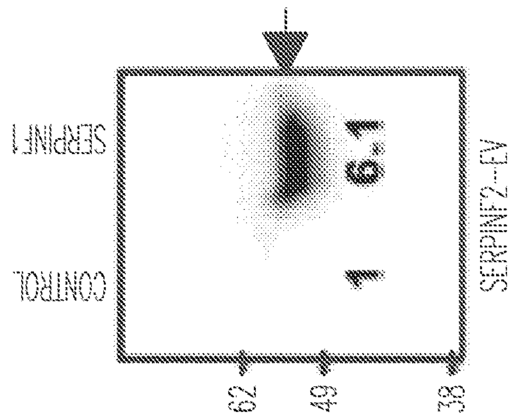
Figure 4B:
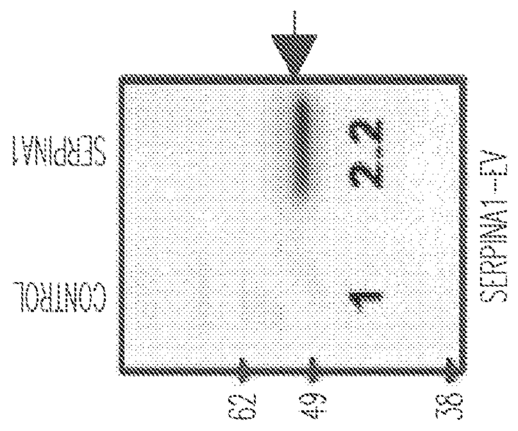
Figure 4E:
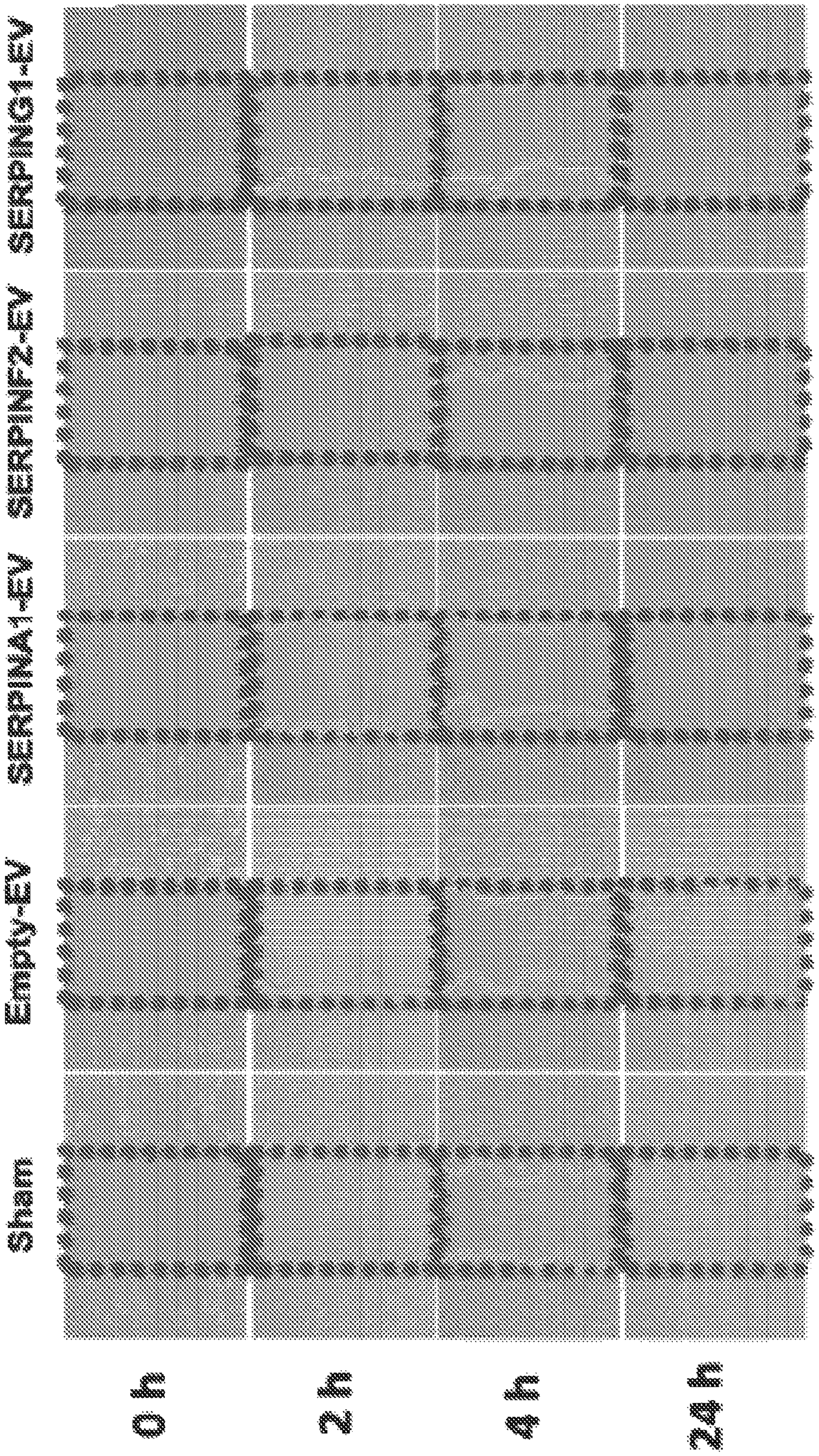
FIG. 4E shows representative images of HaCaT cell closure kinetics.
Figure 4F:
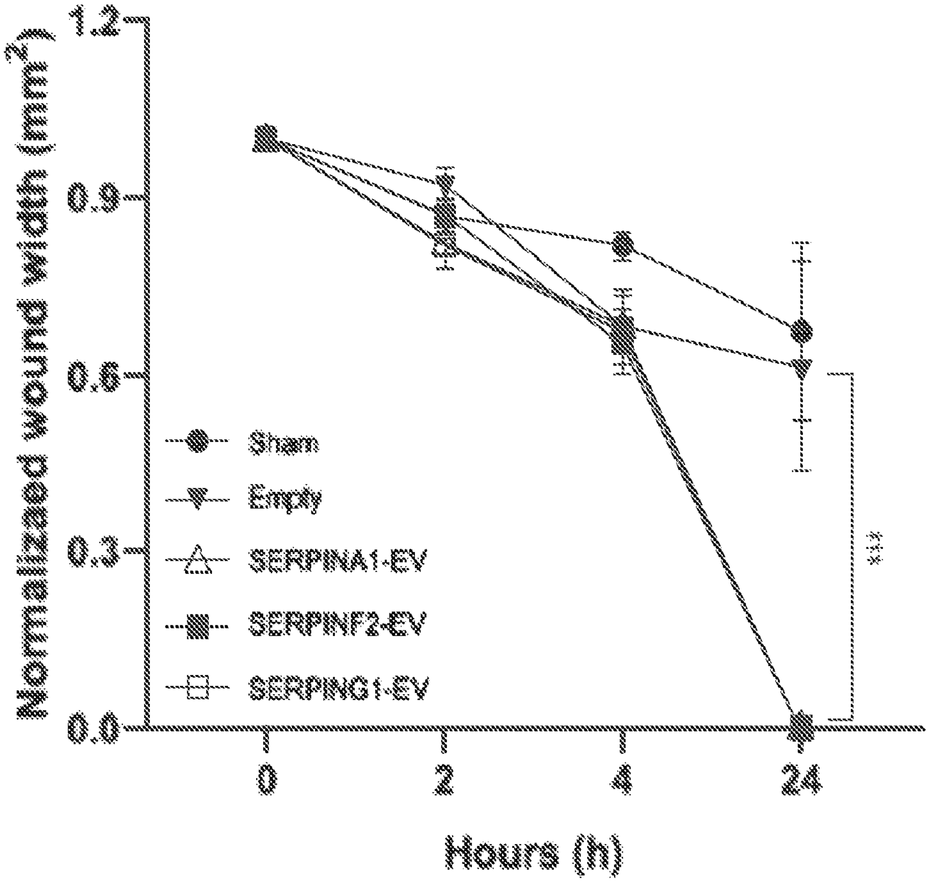
FIG. 4F shows gap closure quantification of HaCaT cells treated with SERPINA1-EVs, SERPINF2-EVs, SERPING1-EVs, vs. empty vector, and sham (PBS). (p-value: ***<0.001, n=6).
Figure 4G:
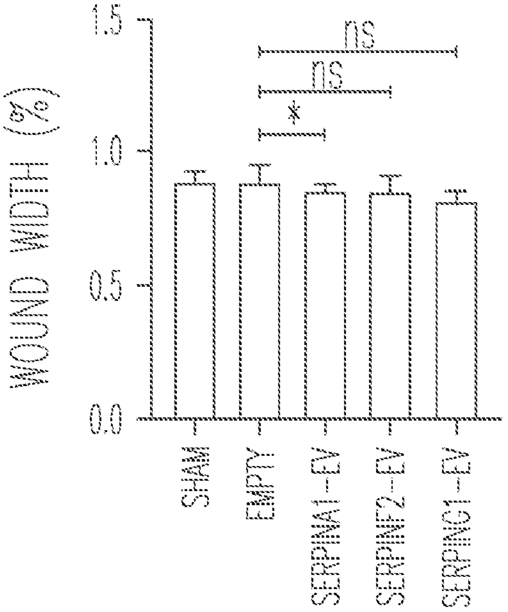
FIG. 4G shows a statical analysis of scratch assay on HaCaT cells by SERPIN-loaded EVs enriched from HEK293 donor cells on 2 h (p-value: **<0.005, *<0.05).
Figure 4H:
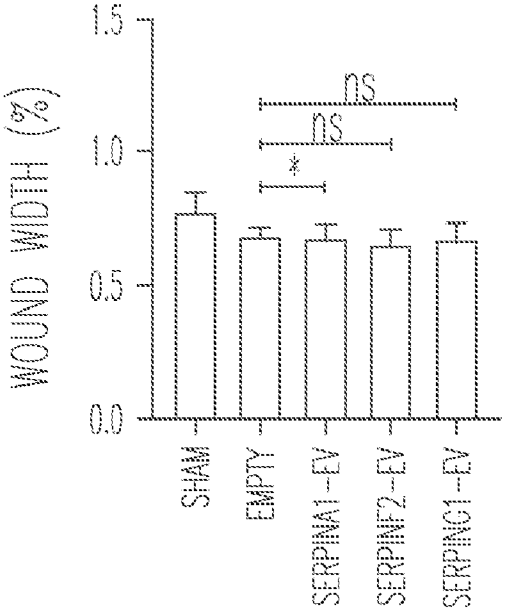
FIG. 4H shows a statical analysis of scratch assay on HaCaT cells by SERPIN-loaded EVs enriched from HEK293 donor cells on 4 h (p-value: **<0.005, *<0.05).
Figure 4I:
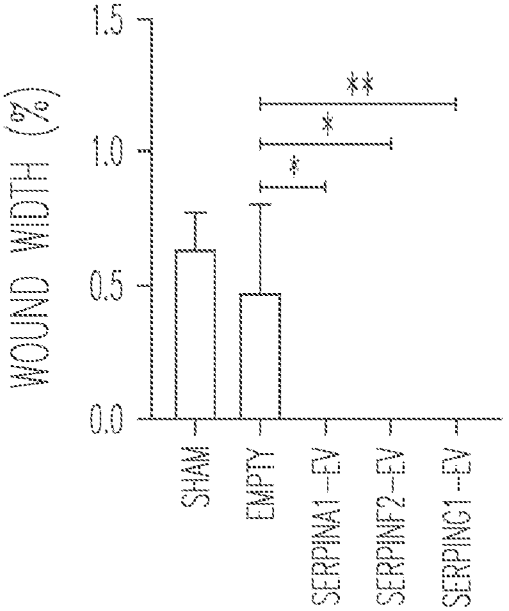
FIG. 4I shows a statical analysis of scratch assay on HaCaT cells by SERPIN-loaded EVs enriched from HEK293 donor cells on 24 h (p-value: **<0.005, *<0.05).

To determine the potential of engineering EV protein payloads as therapeutics in a wound healing model, proteins of interest were expressed as in frame fusions with an amino terminal sequence that incorporated a myristyolation sequence known to lead to the post-translational modification and preferential trafficking of modified proteins into EVs. Focusing first on the loading of a green fluorescent protein reporter expressed as a fusion protein (XP-GFP), lentivirus-mediated gene delivery was used to express XP-GFP in cultured HEK293 cells from which EVs were enriched and subjected to a quantitative analysis to determine EV size, GFP fluorescence, tetraspanin CD81 expression, and uptake into HEK293 cells. These studies established that amino terminal fusions using myristoylation sequences localized proteins to EVs that were capable of delivering protein cargos to 30-50% of the cells treated with EVs as measured by GFP fluorescence. Based on these validations, each of the three Serpins identified as down-regulated in db/db EVs (FIG. 4A) as myristoylated fusion proteins were cloned to generate Serpin-loaded EVs for biochemical and activity testing. Densitometry analysis of immunoblots of EVs enriched from transduced HEK293 cells demonstrated Serpin expression in released EVs (FIGS. 4B-D) compared to EVs from control parental cells. The activity of these Serpin-loaded EVs were then tested in an in vitro model of wound healing based on migration of human HaCaT keratinocyte cells. Following removal of a dividing insert, HaCaT cells were treated once with each engineered EV type (1.20-1.7×$10^5$ particles/μL), and changes in the cell gap quantified (FIG. 4E, F). The kinetics of closure following treatment with Serpin-loaded EVs was significantly accelerated at 24 h for each of the fusion proteins expressing Serpins (SERPINA1, SERPINF2, and SERPING1) compared to the empty vector control (FIGS. 4G-I).

Figure 5A:
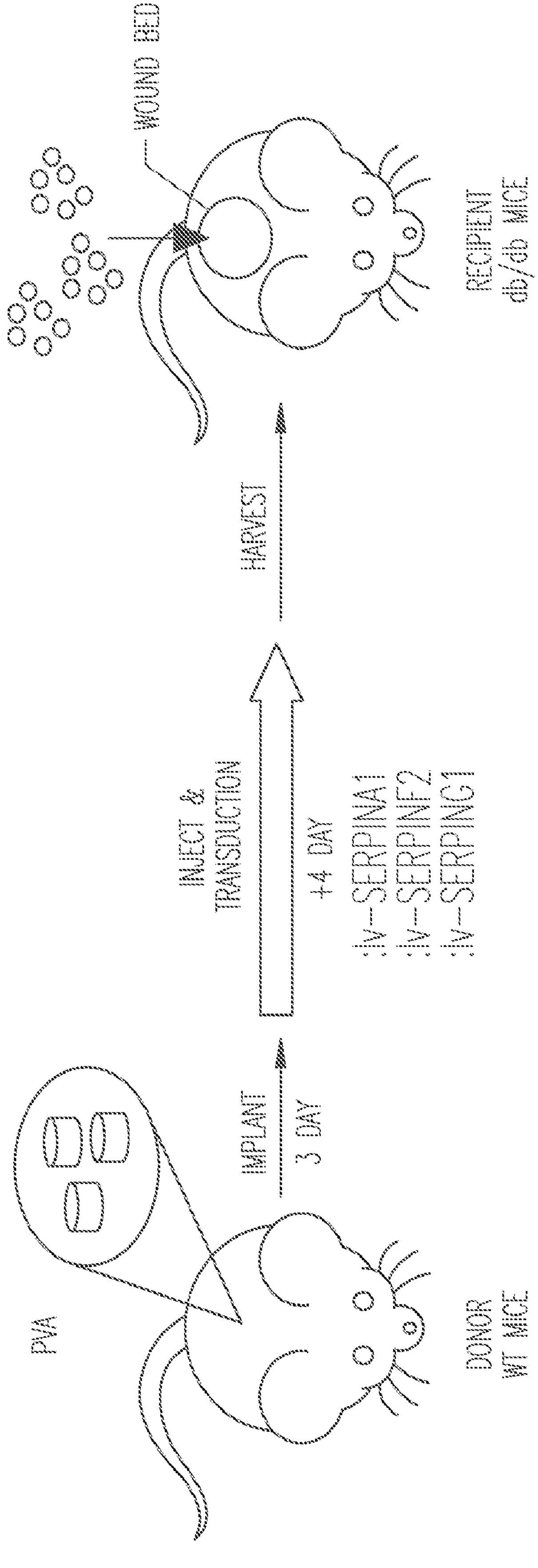
FIG. 5A shows in vivo strategy to transduce cells infiltrating PVA sponge implants and enrich their EVs for assessment of wound closure activity following the expression, release and enrichment of EVs loaded with SERPINA1, SERPINF2, SERPING1, and empty vector controls.
Figure 5B:
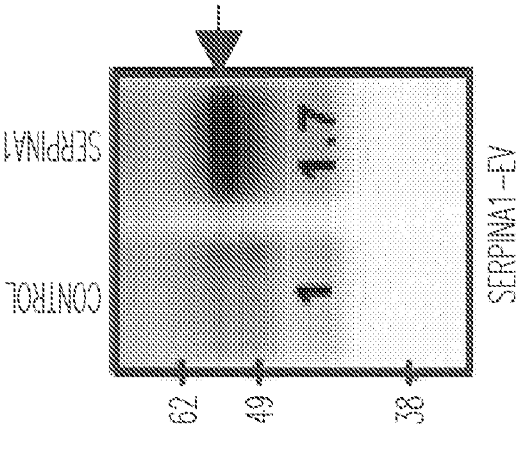
FIGS. 5B-D show validation of Serpin expression in engineered EVs by immunoblotting EVs recovered from implants, with densitometric quantification shown on the blot.
Figure 5C:
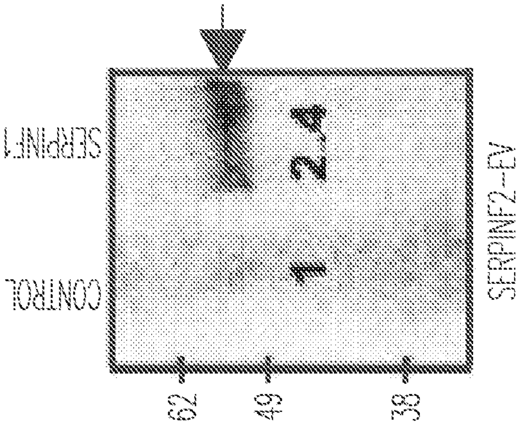
Figure 5D:
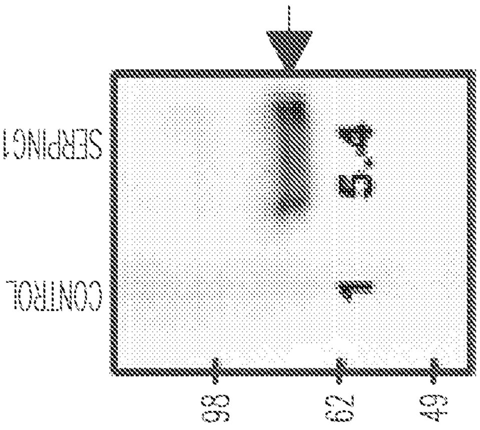
Figure 5E:
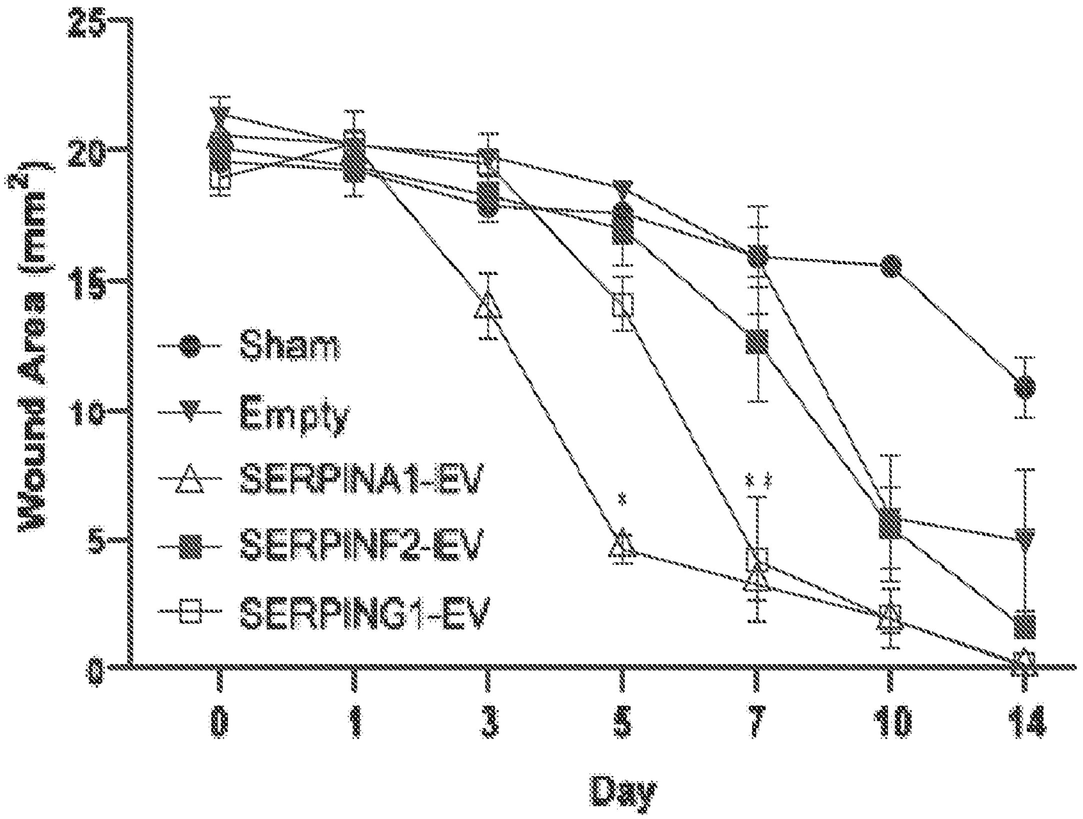
FIG. 5E shows quantification of wound closure kinetics following adoptive transfer in the db/db mouse model of impaired wound healing. (2-way ANOVA, p-value<0.0001 for SERPINA1 and SERPIN G1 vs. empty vector control, n=6 in each arm).
Figure 5F:
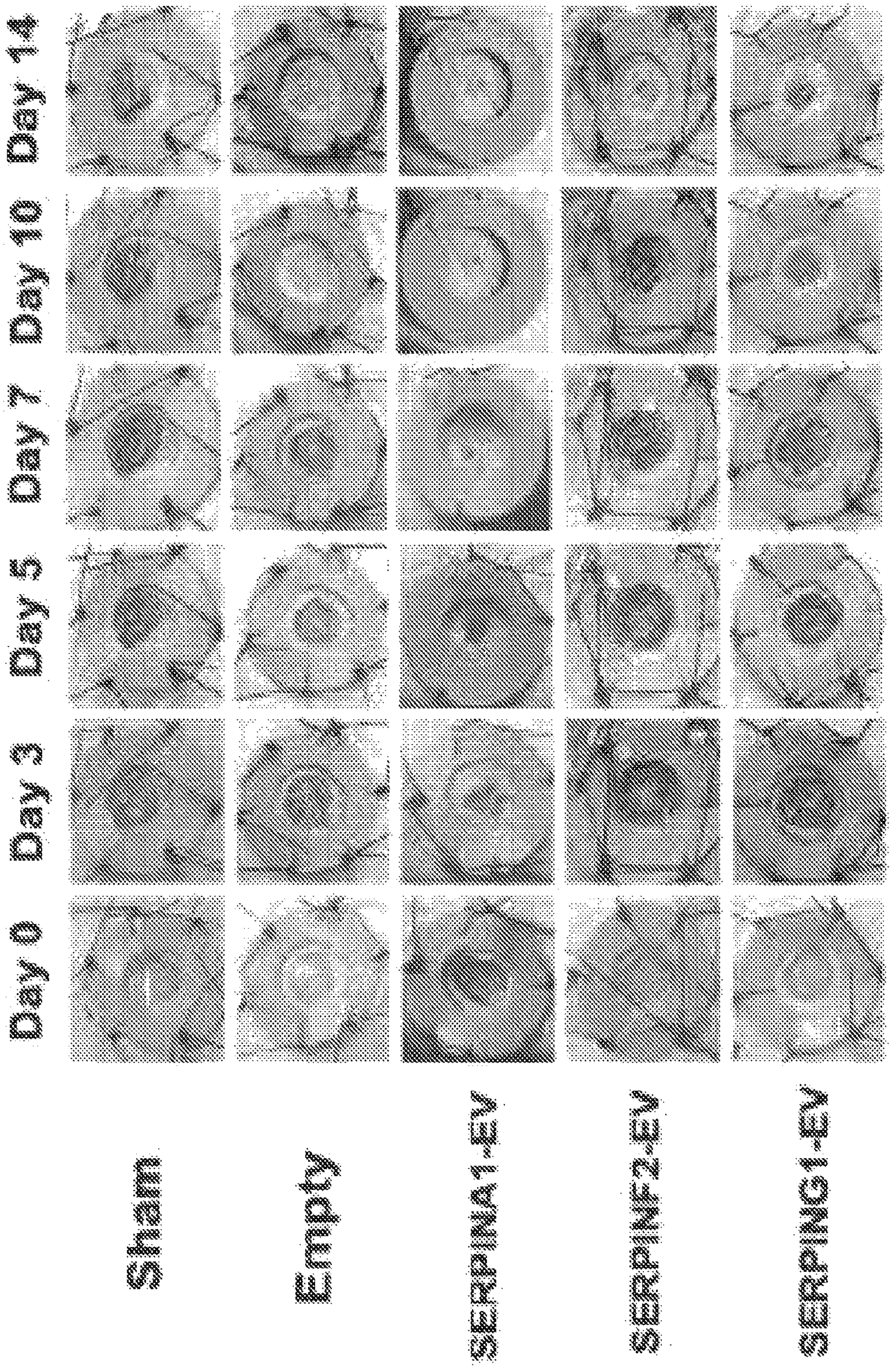
FIG. 5F shows representative images of splinted wounds treated with Serpin-loaded EVs.
Figure 5G:
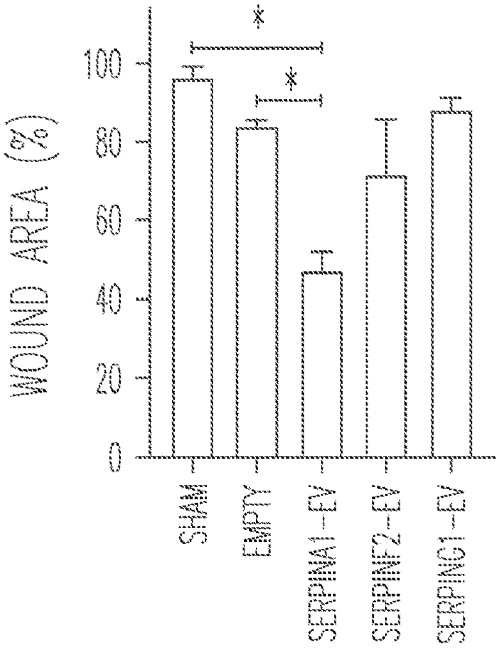
FIG. 5G shows a statical analysis of wound closure efficiency in vivo using SERPINA1-EVs, SERPINF2-EVs, and SERPING1-EVs on Day 3 (p-value: **<0.0001, *<0.001, **<0.005, *<0.05). I Representative images of immunostaining at each time point to demonstrate expression of cytokeratin 14 at Day 5 and 10 post-injury.
Figure 5H:
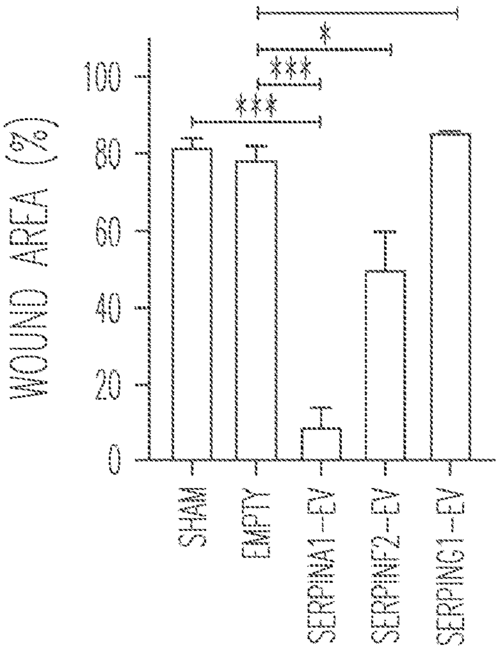
FIG. 5H shows a statical analysis of wound closure efficiency in vivo using SERPINA1-EVs, SERPINF2-EVs, and SERPING1-EVs on Day 5 (p-value: **<0.0001, *<0.001, **<0.005, *<0.05).
Figure 5I:
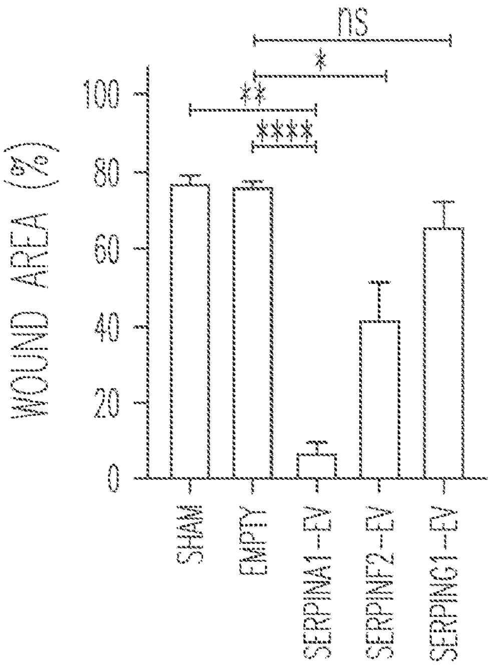
FIG. 5I shows a statical analysis of wound closure efficiency in vivo using SERPINA1-EVs, SERPINF2-EVs, and SERPING1-EVs on Day 7 (p-value: **<0.0001, *<0.001, **<0.005, *<0.05).
Figure 5J:
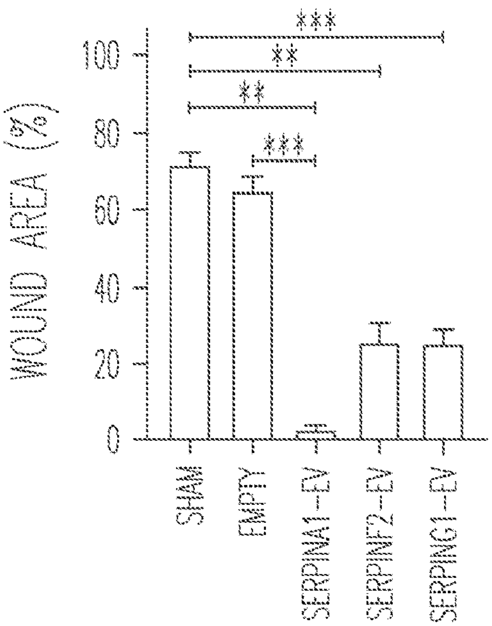
FIG. 5J shows a statical analysis of wound closure efficiency in vivo using SERPINA1-EVs, SERPINF2-EVs, and SERPING1-EVs on Day 10 (p-value: **<0.0001, *<0.001, **<0.005, *<0.05).
Figure 5K:
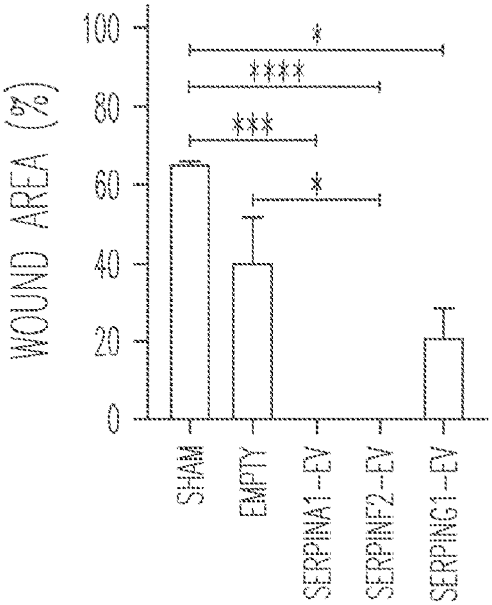
FIG. 5K shows a statical analysis of wound closure efficiency in vivo using SERPINA1-EVs, SERPINF2-EVs, and SERPING1-EVs on Day 14 (p-value: **<0.0001, *<0.001, **<0.005, *<0.05).
Figure 5L:
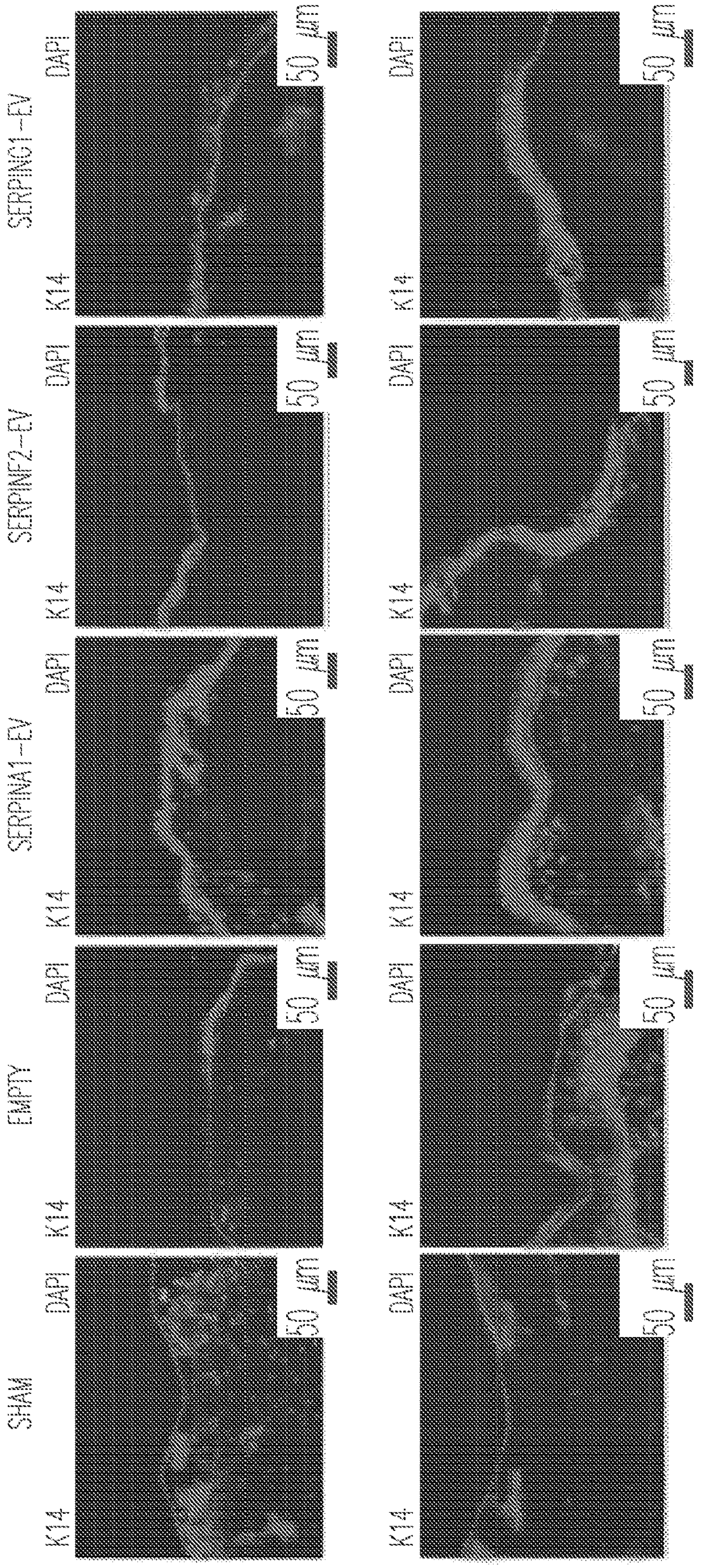
FIG. 5L is representative images of immunostaining at each time point to demonstrate expression of cytokeratin 14 at Day 5 and 10 post-injury.

To determine if Serpin-loaded EVs accelerated tissue repair in an in vivo model of impaired wound closure, a species-matched PVA sponge implant model (FIG. 5A) was used that combines in vivo gene transduction and EV harvest to test EV activity in vivo. In this study PVA infiltrating cells were transduced in vivo with Serpin-expressing lentiviral vectors, and Serpin-loaded EVs were then harvested from the conditioned fluid of cells in the PVA implants. PVA cells were transduced with lentiviruses encoding fusions of SERPINA1, SERPINF2, SERPING1 with the same myristoylation tag used for the in vitro studies and compared with an empty vector control expressing only the tag. These EVs were enriched, counted, and the expression of the appropriate Serpin confirmed and quantified (FIGS. 5B-D). To test the biological activity of the Serpin-loaded EVs, each was tested by adoptive transfer into the splinted full thickness wound model of impaired wound healing using db/db mice as the recipients. In contrast to kinetics of wound closure of PBS-treated (sham) db/db mice, wound closure was significantly accelerated by day 5 and 7 following a single dose treatment with EVs loaded with SERPINA1 and SERPING1, compared to empty vector control EVs (FIG. 5E) that was supported by representative images (FIG. 5F) and statistical analysis (FIGS. 5G-K). To assess the effect of Serpin-loaded EVs on re-epithelialization immunohistochemistry with an anti-cytokeratin 14 (K14) antibody was performed and observed K14 staining within 5 days following treatment with SERPINA1 and SERPING1-loaded EVs compared to empty vector control (FIG. 5L). By Day 10, treatment with Serpins had increased immunostaining compared with sham and empty vector control EVs. Taken together these findings support the development of therapeutic EVs based on an EV loading strategy using fusion proteins and demonstrates the pro-reparative activity of SERPINA1 and SERPING1-loaded EVs in tissue repair.

Discussion

The application of EVs as therapeutics to promote tissue repair highlights their translational potential; however, the molecular mechanisms of EV action remain poorly understood. Questions remain regarding what factors mediate their efficacy, the identity of relevant payloads, and how EV biology is altered in a chronic vs. normal wound bed. It had been previously shown that dysregulation of EV biogenesis pathways blocks wound repair by affecting protein payload and immune cell recruitment relevant to the resolution of the inflammation phase wound repair. Here the focus is on a genetically defined mouse model of Type 2 diabetes with impaired wound healing to assess EV biology in this process. It was not that wildtype EVs accelerate wound closure compared to EVs from diabetic donors. Proteomic analysis of EVs isolated from diabetic mice have a deficit in the expression of a family of serine protease inhibitors, specifically Serpins A1 (anti-trypsin), Serpin F2 (anti-plasmin), and Serpin G1 (plasma protease C1 inhibitor). Given the role of Serpin A1 in inactivating elastases and Serpin F2 in regulating fibrinolysis by inactivating plasmin, and Serpin G1 in inhibiting the complement response, it is proposed that EVs are nanocarriers of key regulatory elements responsible for coordinating hemostasis, immune cell activation and the resolution phase of wound healing. It has been shown that re-expression of the specific Serpins in EVs that are deficient in diabetic mice accelerated wound closure in an adoptive transfer strategy, and establishes the potential for Serpins to coordinate tissue repair (FIG. 6).

Dysfunction of immune function, fibrosis, and a non-migratory epidermis are all hallmarks of the impaired wound healing responses observed in diabetic patients, including diabetic foot ulcers, for which there are limited effective therapies. For example, diabetic patients fail to activate key transcriptional networks in neutrophils and macrophages that are recapitulated in diabetic mouse models. These findings suggest that the lack of coordinated signaling and immune responses contribute to impaired re-epithelialization and delayed wound closure. In these examples, biochemical mediators identified as down-regulated in the diabetic wound can be re-expressed to assess their potential to rescue tissue repair in chronic wounds as it has been demonstrated here with Serpin-loaded EVs.

The multiple overlapping phases of hemostasis, inflammation, proliferation, and remodeling in wound healing are both multicellular and highly coordinated, suggesting that therapeutic approaches are needed that address defects in intercellular signaling between cells that are not otherwise in direct contact. The use of the PVA sponge to generate donor EVs takes advantage of the similar immune responses with the inflammation phase of wound healing and avoids the limitations of classic cell culture methods based on cultured single cell types on plastic in the presence of serum. For the evaluation of EVs in the treatment of impaired cutaneous wound healing, normal EVs have been generally collected from cultured human cells, with recent studies showing that delivery of specific molecules affects wound closure in the diabetic model.

Based on evidence that fibrinolysis and changes in the extracellular matrix (ECM) scaffolding are essential to the coordinated resolution of the inflammation phase and re-epithelialization, the findings presented herein support a role for specific protease inhibitors in these processes. For example, protease inhibitors such as Serpins are critical molecular switches in ECM remodeling cascades that affect the recruitment of immune cells and re-epithelialization through a combination of direct contact and indirect intercellular signaling. Based on the pro-reparative potential of EVs in the diabetic wound, the analysis presented herein of isolated wildtype and diabetic EVs has identified distinct protein payloads and biological activities in mediating wound repair. The impaired expression of protease inhibitors in diabetic wound EVs underscores the importance of specific proteases that mediate remodeling of the ECM, drive the recruitment and activation of immune cells in wound closure, and are indicative of a more general dysfunction of proteases in diabetic wounds.

For example, Serpin A1 encodes the alpha1-proteinase inhibitor (α1PI), which acts upon trypsin as well as neutrophil elastases. Diabetic wounds have increased elastase associated with infection and worsening of ulcers, consistent with the observation of decreased levels of the SerpinA1/α1PI elastase inhibitor in diabetic wound EVs. While the mechanisms of EV-mediated SerpinA1 have yet to be elucidated, SerpinA1/α1PI also has non-enzymatic activity in its ability to bind to the cell surface and promote migration. Surface binding of EVs, especially at the leading edge where membrane-bound EVs loaded with ECM-remodeling protease/protease inhibitors, can enhance cell migration by modifying intracellular actin re-organization that promotes directional cell adhesion. Other examples of the pathogenesis of reduced SerpinA1/α1PI levels include increased neutrophil elastase in the bloodstream leading to acute inflammation, degradation of lung elasticity, and liver cirrhosis.

The decreased levels of Serpin F2/antiplasmin observed in EVs in the diabetic wound support the role for factors regulating coagulation and fibrinolysis in wound healing. In wound healing, mice lacking plasminogen, the zymogen form of plasmin, tissue plasminogen activator or urokinase plasminogen activator all have impaired wound healing responses. While free Serpin F2/antiplasmin inhibits plasmin formation, the fibrin-bound form regulates clot lysis. Studies of mice lacking Serpin F2/antiplasmin show accelerated angiogenesis and wound closure further supporting a role for the fibrinolytic cascade in regulating wound closure kinetics, although the timing and localization of specific targets remain poorly understood. Therefore, wound healing disorders may respond to increases in protease inhibitors such as Serpin F2/antiplasmin that accelerate fibrinolysis and promote conversion of a wound microenvironment from pro-inflammatory to pro-resolution and increased wound closure.

Serpin G1/C1-inhibitor is an acute-phase protein that increases in the circulation in response to injury, and functions to inhibit the complement system. Deficiency in Serpin G1/C1-inhibitor also permits kallikrein activation, and the production of the vasoactive peptide bradykinin. In the wound bed, administration of a Serpin G1/C1-inhibitor reduces local inflammation and capillary leakage, although the acceleration of wound closure may depend on the duration of Serpin G1/C1-inhibitor administration. With Serpins often classified as acute phase proteins that regulate inflammation, expressing specific Serpins in EVs may promote wound closure by delivering enzyme inhibitors in EVs that have an EV-dependent tropism for specific microenvironments of the wound bed. For example, elastase levels in diabetic ulcer tissue were significantly higher in wounds with infections and presented with a delayed wound healing profile. Moreover, EVs delivering enzymes that regulate the remodeling of ECM can localize protease inhibitors at the interface of plasma membrane and release protein payloads at membrane domains regulating the leading edge of migrating cells.

The rationale for the delivery of EVs loaded with specific protein payloads is based on the identification of specific Serpins that are down-regulated in the diabetic EVs, which can then be tested for their capacity to restore wound closure kinetics of a wild type full thickness wound. The strategy uses lentiviral constructs to express a target protein as a fusion with a membrane domain that traffics proteins to EVs and anchors them to the membrane. Membrane domains that mediate the trafficking of protein payloads into EVs based on a myristoylation domain have similarities with viral budding that can be exploited for delivery of custom EV protein payloads.

EV-based therapies have emerged as a significant area of interest in the treatment of ischemia, infection, impaired wound healing, and cancer, however, none are FDA-approved to date. The over-arching concept behind the development of EV-based therapeutics is their potential as stable delivery vehicles of payloads that regulate intercellular signaling, especially when compared to small molecules in solution or cell therapy. EVs are complex in terms of the range of their protein and nucleic acid payloads, and heterogenous in terms of the different populations of EVs present in a multi-cellular microenvironment where a given cell type may release different EVs depending on its metabolism and activation state. As in previous EV proteomic studies, proteomics were used to identify proteins that are differentially expressed in EVs which in this study it has been shown can be rescued using a re-expression system. The use of a species and strain-matched donors for the collection EVs for the analysis of the effect of the diabetic host on their EV payload is essential for the determination of their ability to promote wound closure following adoptive transfer into a full thickness chronic wound.

CONCLUSIONS

The discovery of a deficiency of Serpin expression in the EVs of diabetic mice led to the hypothesis that over-expression of such Serpins in engineered EVs could be used to rescue impaired wound healing. The combination of target discovery leading to the development of Serpin-loaded EVs established the biological activity of engineered Serpins with applications that may well extend beyond the molecular targets and injury models tested here.

Methods

Mice, PVA Sponge Implants and Wound Healing Assays

All animal experiment were conducted in accordance with the protocols approved by the Institutional Animal Care and Use Committee of the University of California, San Diego. Male 10-16-week-old C57BL/6J mice (#JAX 0664) and Leprdb/db mice (JAX 0697) were maintained on a 12 h light/dark cycle. Subcutaneous implants of sterile polyvinyl alcohol (PVA) sponges (PVA unlimited, Warsaw, IN, USA) inserted (n=3 per site) in dorsum of each animal and the surgical site closed with nylon monofilament suture (#MV-663-V-19 mm, Oasis, IL, USA). Animals recovered in the presence of sufficient food and water supply. Mice bearing PVA sponges were incubated as indicated for up to 14 days, the sponges removed under anesthesia, transferred into 500 μl of PBS in a microtube, and the sponges briefly compressed with a forceps 3-4 times to release cells and EVs from the sponge. The sponges were then removed, and cells separated from the PVA fluid by centrifugation at 300×g for 5 min for analysis by flow cytometry and quantitative PCR, while EVs were enriched from the supernatant for in vitro testing as described below and tested in adoptive transfer assays into full thickness wounds in naïve db/db mice. For these assessments of EV activity upon the kinetics of wound healing assay in the db/db model, hair was removed, a full thickness 4 mm punch made (#P450, Acuderm inc., FL, USA), the site splinted with silicone ring (Thickness: 0.5 mm, outside diameter: 12 mm, inside diameter: 6 mm) (#33350174, MCS, Mableton, GA, USA) and the ring immobilized with nylon suture as previously described were. EVs were added to the wound site in 10-50 µL, covered with Tegaderm (#1622w, 3M, Maplewood, MN, USA), and the wound site imaged daily with a digital camera (Galaxy 10e, 1200 pixels, AF, F1.5/F2.4 super speed dual pixel, Samsung, Seoul, Korea) and analyzed by Image J (1.53e version, National Institutes of Health, Bethesda, USA). Hematoxylin and eosin-stained tissue sections of skin were prepared from formaldehyde fixed paraffin embedded, and cryosections prepared in Tissue-Tek® OCT compound (Cat #4583, Sakura® Finetek, Torrance, CA, USA), stained with Cytokeratin 14 antibodies (Cat #10143-1-AP, Proteintech, Rosemont, IL, USA) and imaged with laser scanning confocal microscope (ECLIPSE Ti2, Nikon Instruments Inc. Melville, NY, USA). These EV assays were used for the assessment of WT vs db/db EV activity as well as for the analysis of EV engineered to express specific Serpins as described below. In both studies, EVs were prepared from mice bearing PVA sponge implants, enriched, quantified and then adoptively transferred to full thickness splinted wounds as described above.

Flow Cytometry

For the analysis of cells recruited to the PVA sponge model used for the harvest of EVs, cells were subjected to flow cytometry using Fc block (Cat #130-092-575, Miltenyi Biotec, San Diego, CA, USA), followed by staining with antibodies specific for the following immune cell markers from Miltenyi Biotec. (CD11b, #130-109-287; CD11c, #130-110-840; CD45, #130-110-803; CD44, #130-119-127; F4/80, #130-102-422; Gr1, #130-102-233; Ly6G, #130-107-912, Ly6C, #130-123-796, MHCII, #130-119-122; CD4, #130-118-696, and CD3, #130-117-788). Propidium iodide (#130-093-233, Miltenyi Biotec, San Diego, CA, USA) was used to exclude dead cells. Isotype antibodies were also used for all fluorescence with species matched. (VioBlue/PacBlue, #130-113-454; VioGreen/BV510, #130-113-456; FITC, #130-113-449; PE, #130-113-450; PE-Vio770, #130-113-452; APC, #130-113-446; and APC-Vio770/Fire750, #130-113-447, Miltenyi Biotec, CA, USA). All flow cytometry was performed on a MACSQuant 10 instrument (Miltenyi Biotec, San Diego, CA, USA) and analyzed using FlowJo software (Version 10.7.1, Becton, Dickinson and Company, Franklin Lakes, NJ, USA).

Isolation of EVs

EV isolation from PVA sponge implants was based on density gradient ultracentrifuges as previously described, with an initial spin of 10,000×g for 30 min at 4° C. to separate EVs from the PVA fluid. Opti prep gradient (#D1556, Sigma Aldrich, CA, USA), was prepared as 8% (1.068 g/ml), 10% (1.078 g/ml), 14% (1.098 g/ml), 20% (1.127 g/ml), 26% (1.156 g/ml), and 30% (1.175 g/ml) solutions layers overlaid with supernatant in polycarbonate ultracentrifuge tube (#343778, Beckman coulter, CA, USA) (Rotor #TS55, k factor: 50 k, Beckman coulter), and fractionated at 259,000×g (Accel: 4/Decel: 9) for 2 h in a Beckman Optima Max-XP Ultracentrifuge. After centrifugation, 10×100 µl fractions were collected, protein concentration determined by BCA assay (#23227, Thermo Fisher Scientific, Waltham, MA, USA). For assays of protein expression, EVs were solubilized in RIPA lysis buffer (#89901, Thermo Fisher Scientific), while for quantification of EV size, concentration, mass spectrometry, vFC or biological activity, EVs from control and experimental groups were normalized based on concentration as indicated.

EVs isolated from cultured media for in vitro assays was performed using Exoquick kit (#EQULTRA-20A-1, SBI, CA, USA) and following manufacturer's recommendations. Briefly, cell culture medium was centrifuged at 3,000×g for 15 min to remove cell debris, supernatant transferred to a new tube and incubated overnight at 4° C. with Exoquick. The Exoquick/media mixture was centrifuged at 3,000×g for 10 min, the supernatant aspirated, and the pellet resuspended in PBS for subsequent concentration, sizing, immunoblotting and biological activity studies.

Quantification of EVs and Concentration and Size Distribution by vFRed Analysis

EV samples diluted by PBS, and stained with a fluorogenic membrane stain (vFRed, Cellarcus Biosciences), a cytoplasmic stain (CFSE, Cellarcus) and EV surface markers in a total volume of 50 µl in a 96 well v bottom plate for 1 h at ambient temperature, according to manufacturer's instructions. The optimal concentrations of antibody and other reagents was determined by the manufacturer via titration and provided at 10× the final staining concentration. Stained samples were diluted 1000-fold in vesicle staining buffer and analyzed on the flow cytometer. The dilutions series protocol determines the EV concentration, assay dynamic range, and the optimal dilution for subsequent cargo analysis.

Transmission Electron Microscopy

For the imaging of EVs by transmission electron microscopy (TEM) on grids, the PELCO easiGlow system (91000S, Ted Pella, Inc) was using for hydrophilization onto grids (Cat #01754-F, Formvar, 200 mesh, copper, Ted Pella, Inc., Redding, CA, USA). Grids were washed and stained with uranyl acetate, and imaged with a Jeol 1400 plus TEM at 80 KeV (Jeol USA, Peabody, MA, USA).

Sample Preparation and LC-Mass Spectrometry

EVs samples from PVA implants were isolated by density ultracentrifugation as described above and analyzed in the Biomolecular and Proteomics Mass Spectrometry Facility at UCSD. For each sample, guanidine-HCl was added to each sample to final concentration of 6 M, boiled for 10 min and cooled at room temperature for 5 min, with this cycle repeated three times. Following methanol precipitation and removal of the supernatant, the pellet was suspended in 8M Urea in 100 mM (Tris pH 8.0). Samples were brought to a final concentration of 10 mM TCEP (2-carboxyethyl phosphine) and 40 mM Chloro-acetamide solution. Three volumes of 50 mM Tris pH 8.0 were added to the sample to reduce the final urea concentration to 2 M. Trypsin was add (1:50 ratio), incubated at 37° C. for 12 h, samples acidified using TFA (0.5% TFA final concentration) and desalted using C18-StageTips (#87782, Thermo Fisher) as described by the manufacturer protocol. The peptide concentration of sample was measured using BCA after resuspension in TMT buffer. For high pH fractionation, the Pierce™ High pH Reversed Phase Peptide Fractionation Kit (#84868, Thermo Fisher) to generate 8 unique peptide fractions that were analyzed by ultra-high-pressure liquid chromatography (UPLC, Thermo Dionex UltiMate™ 3000 RSLC nano System) (#ULTIM3000RSLCNANO, Thermo Fisher) coupled with tandem mass spectroscopy (LC-MS/MS) using nano spray ionization. The nano-spray ionization experiments were performed using an Orbitrap fusion Lumos hybrid mass spectrometer (Model #IQLAAEGAAPFADBMBHQ, Thermo Fisher) interfaced with nanoscale reversed-phase UPLC using a 25 cm, 75-micron ID glass capillary packed with 1.7-µm C18 (130) BEH™ beads (Waters corporation). Peptides were eluted from the C18 column into the mass spectrometer using a linear gradient (5-80%) of ACN (Acetonitrile) at a flow rate of 375 µl/min for 120 min. The buffers used to create the ACN gradient were: Buffer A (98% H2O, 2% ACN, 0.1% formic acid) and Buffer B (100% ACN, 0.1% formic acid). Mass spectrometer parameters are as follows; an MS1 survey scan using the orbitrap detector (mass range (m/z): 400-1500 (using quadrupole isolation), 60000 resolution setting, spray voltage of 2200 V, Ion transfer tube temperature of 290° C., AGC target of 400000, and maximum injection time of 50 ms) was followed by data dependent scans (top speed for most intense ions, with charge state set to only include +2-5 ions, and 5 sec exclusion time, while selecting ions with minimal intensities of 50,000 at in which the collision event was carried out in the high energy collision cell (HCD Collision Energy of 38%) and the first quadrupole isolation window was set at 0.8 (m/z). The fragment masses were analyzed in the orbitrap detector (mass range (m/z) by automatic scan with first scan at m/z=100. The resolution was set at 30000 resolutions. The AGC Target set to 30000, and maximum injection time was 54 m-sec. Protein identification and quantification was carried out using Peaks Studio 8.5 (Bioinformatics solutions Inc., Canada).

Western Blot

All EVs subjected to immunoblotting were quantified by BCA assay kit (#23225, Thermo Fisher), samples prepared in NuPAGE™ LDS Sample Buffer (#NP0008, Thermo Fisher), separated using the 12% Bis-Tris Mini Gel (#NP0342BOX, Thermo Fisher), transferred to PVDF membrane (#LC2005, 0.45 μm, 8.3×7.3 cm, Thermo Fisher), and blocked with 3% Nonfat Dry Milk Cell (NFDM) (Cat #9999, CST, MA, USA) in 1λ Tris-buffered saline (#9997, CST, MA, USA) with 0.05% Tween 20. Primary antibodies used were CD81 (#10037, CST), CD63 (#PA5-92370, Invitrogen, USA), CD9 (#PA-5-85955, Invitrogen), Alix (#92880, CST), SERPINA1 (#TA500374s, Origene, USA), SERPINF2 (#PA5-81014, Thermo Fisher), and SERPING1 (#PA5-81015, Thermo Fisher) at a 1/1000 dilution. Anti-rabbit IgG, HRP-linked (#7074, CST) or anti-mouse IgG, HRP-linked antibodies at 1/1000 dilution (Cat #7076, CST, USA) were used as secondary antibodies, and blot incubated with Pierce™ ECL western blotting substrate reagent (#32209, Thermo Fisher), blots imaged with a Xenogen IVIS-Lumina (Caliper Life Sciences Inc., Hopkinton, MA, USA) and the band intensities quantified using Living Image software (Ver.4.3.1, Caliper Life Sciences).

Cloning and Lentivirus Production

Lenti-X 293T cells (#632180, TakaraBio) were used for the production of lentivirus based on Lenti-XPack vectors (System Biosciences, Palo Alto, CA) that contained the EV signal peptides as an N-terminal fusion with a multiple cloning site (pLenti-XPack-MCS (#XPAK710PA-1) or as fusion with GFP (pLenti-XPack-GFP, #XPAK510PA-1). Primer design tools from TAKARA (https://www.takarabio.com/learning-centers/cloning/primer-design-and-other-tools) were used to amplify SERPIN genes from cDNAs (Origene) encoding human SERPINA1 (#RC202082), SERPINF2 (#RC228342) or SERPING1 (#RC203767) flanked by Xho I and NotI restriction enzyme sites for cloning into pLenti-XPack-MCS vector. The following primers were used for SERPINA 1-F (5'-GCA AAG ATG CCT CGA GGA TGC CGT CTT CTG TCT CGT G-3') and SERPINA1-R (5'-AGA ATT CTC GCG GCC GCT TAT TTT TGG GTG GGA TTC ACC AC-3'); SERPINF2-F (5'-GCA AAG ATG CCT CGA GGA TGG CGC TGC TCT GGG G-3') and SERPINF2-R (5'-AGA ATT CTC GCG GCC GCT CAC TTG GGG CTG CCA AAC TGG-3') and SERPING1-F (5'-GCA AAG ATG CCT CGA GGA TGG CCT CCA GGC TGA CC-3') and -SERPING1-R (5'-AGA ATT CTC GCG GCC GCT CAG GCC CTG GGG TCA TAT ACT CG-3'). PCR fragments were linearized and cloned using the In-fusion kit (All In-fusion mix Plus, #638917, TAKARA). The Lenti-vpak packaging kit (#TR30037, OriGene Technologies Inc, Rockville, MD, USA) was used for virus production, with lentivirus being collected and concentrated from conditioned media using the Lenti concentrator (#TR30026, OriGene Technologies Inc) and quantified using Lenti-X GoStix Plus (#631280, TaKaRa Bio USA Inc, San Jose, CA, USA) that measures the expression of lentiviral p24 protein using GoStix Value software (Takara). Lentiviral stocks of matched titer were used for the subsequent transduction of either human HEK293T cells from which EVs would be collected for the treatment of HaCaT cells. PVA sponges were implanted three days prior to injection of the lentivirus into the sponge implants to facilitate in vivo transduction of infiltrated leukocytes. After an additional 4 days to allow for gene expression, cells and fluid from the PVA implant were harvested with EVs enriched from the fluid and adoptively transferred to full thickness wounds to assess activity by wound closure analysis as described above.

Serpin-Loaded EV Activity Cell Migration Assay

HEK293T (CRL-1573, ATCC, Bethesda, MD) cells were transduced with lentivirus (10,000 to 15,000 particles), incubated for 48 h in serum complete media, cells then washed with PBS and the media replaced with a serum-free medium for an additional 24 h. From this serum free media, EVs were concentrated, quantified, and immunoblotted as described above prior to testing in a migration assay using HaCaT cells cultured on 2-well dishes (#81176, Ibidi, Gräfelfing, Germany). After 24 h seeding of cells, an insert was removed, the cell culture media replaced with EV containing media as described, cells imaged over 24 h using a CCD camera (Retiga R6, Teledyne photometrics, Tucson, AZ, USA) on an Olympus IX70 microscope to measure changes in cell migration. All images analyzed using OCULAR v1.0.3.110 software and Image J.

Statistical Analysis

All statistical analyses were performed with Prism 6.0 (Graph pad Software, La Jolla, CA, USA). Descriptive results of continuous variables were expressed as the mean±standard deviation (SD) for normally distributed variables. Differences between different groups were compared by ANOVA for analysis of two or more groups in the kinetic studies, and Student's t-test for pairwise comparisons with p-values indicated as **<0.0001, *<0.001, **<0.005, *<0.05 considered to be statistically significant. All statistical analyzes and representative images are presented as observed in at least 3 independent experiments.

What is claimed is:

1. A pro-reparative extracellular vesicle (EV) composition comprising: at least one fusion protein located inside the EV, the at least one fusion protein having pro-reparative biological activity in at least one of promoting wound healing and tissue regeneration, wherein the at least one fusion protein comprises a serine protease inhibitor.

2. The pro-reparative EV composition of claim 1, wherein the protein comprised in the fusion protein is downregulated or dysregulated in diabetic wounds or models of impaired wound healing.

3. The pro-reparative EV composition of claim 1, wherein the protein comprised in the fusion protein regulates a protease.

4. The pro-reparative EV composition of claim 1, wherein the at least one fusion protein is myristoylated.

5. The pro-reparative EV composition of claim 4, wherein the protein comprised in the myristoylated protein is absent in extracellular vesicles of a subject suffering from at least one of obesity, diabetes, and end-stage renal failure.

6. The pro-reparative EV composition of claim 1, wherein the serine protease inhibitor is a serine protease inhibitor belonging to the serpin family of serine protease inhibitors.

7. The pro-reparative EV composition of claim 1, wherein the at least one fusion protein comprises at least one of serpin A1, serpin F2, and serpin G1.

8. The pro-reparative EV composition of claim 1, wherein the size of the EV is less than about 250 nm.

9. The pro-reparative EV composition of claim 1, wherein the size of the EV is between about 50 nm and about 250 nm.

10. The pro-reparative EV composition of claim 1, wherein the size of the EV is between about 80 nm and about 100 nm.

11. The pro-reparative EV composition of claim 1, wherein the composition comprises a population of EVs having a size ranging between about 50 nm and about 250 nm.

12. The pro-reparative EV composition of claim 1, wherein the composition comprises a population of EVs having a size ranging between about 80 nm and about 100 nm.

13. The pro-reparative EV composition of claim 1, wherein the EV does not comprise a nucleic acid.

14. The pro-reparative EV composition of claim 1, further comprising a pharmaceutically acceptable diluent, carrier, or excipient.

15. A kit comprising the pro-reparative EV composition of claim 1.

16. A method of promoting wound healing in a subject suffering from at least one of obesity, diabetes, and end-stage renal failure, the method comprising administering a therapeutically effective amount of the pro-reparative EVs of claim 1 to a wound of the subject.

17. The method of claim 16, wherein the wound is a chronic wound.

18. The method of claim 16, wherein the pro-reparative EVs accelerate closure of a chronic wound.

19. A method of reversing the inhibitory activity of at least one of elastase, plasmin, and complement in a subject suffering from at least one of obesity, diabetes, and end-stage renal failure, the method comprising administering a therapeutically effective amount of the pro-reparative EV composition of claim 1.

* * * * *